United States Patent
Bennett et al.

(10) Patent No.: US 9,351,973 B2
(45) Date of Patent: May 31, 2016

(54) PYRAZOLOPYRIDYL COMPOUNDS AS ALDOSTERONE SYNTHASE INHIBITORS

(71) Applicants: D. Jonathan Bennett, Boston, MA (US); Jaiqiang Cai, Glasgow (GB); Emma Carswell, Great Shelford (GB); Andrew Cooke, Doylestown, PA (US); Scott B. Hoyt, Hoboken, NJ (US); Clare London, Chatham, NJ (US); John MacLean, Kilmarnock (GB); Min K. Park, Whippany, NJ (US); Paul Ratcliffe, Aarcher (DE); Yusheng Xiong, Plainsboro, NJ (US); Swapan Kumar Samanta, Nandi Layout (IN); Bheemashankar A. Kulkarni, Rajajinagar (IN)

(72) Inventors: D. Jonathan Bennett, Boston, MA (US); Jaiqiang Cai, Glasgow (GB); Emma Carswell, Great Shelford (GB); Andrew Cooke, Doylestown, PA (US); Scott B. Hoyt, Hoboken, NJ (US); Clare London, Chatham, NJ (US); John MacLean, Kilmarnock (GB); Min K. Park, Whippany, NJ (US); Paul Ratcliffe, Aarcher (DE); Yusheng Xiong, Plainsboro, NJ (US); Swapan Kumar Samanta, Nandi Layout (IN); Bheemashankar A. Kulkarni, Rajajinagar (IN)

(73) Assignee: Merck Sharp & Dohme Corp., Rahway, NJ (US)

( * ) Notice: Subject to any disclaimer, the term of this patent is extended or adjusted under 35 U.S.C. 154(b) by 31 days.

(21) Appl. No.: 14/346,518

(22) PCT Filed: Sep. 17, 2012

(86) PCT No.: PCT/US2012/055699
§ 371 (c)(1),
(2) Date: Mar. 21, 2014

(87) PCT Pub. No.: WO2013/043521
PCT Pub. Date: Mar. 28, 2013

(65) Prior Publication Data
US 2014/0288094 A1    Sep. 25, 2014

Related U.S. Application Data

(60) Provisional application No. 61/537,928, filed on Sep. 22, 2011.

(51) Int. Cl.
| | | |
|---|---|---|
| C07D 471/04 | (2006.01) |
| A61K 31/437 | (2006.01) |
| C07D 487/04 | (2006.01) |
| A61K 31/519 | (2006.01) |
| A61P 9/12 | (2006.01) |
| A61P 13/12 | (2006.01) |
| A61P 9/00 | (2006.01) |
| A61P 9/10 | (2006.01) |
| A61P 1/16 | (2006.01) |

(52) U.S. Cl.
CPC ............. *A61K 31/519* (2013.01); *A61K 31/437* (2013.01); *C07D 471/04* (2013.01); *C07D 487/04* (2013.01)

(58) Field of Classification Search
CPC ........................... C07D 471/04; A61K 31/437
See application file for complete search history.

(56) References Cited

U.S. PATENT DOCUMENTS

| | | | |
|---|---|---|---|
| 7,199,120 | B2 | 4/2007 | Gudmundsson et al. |
| 7,199,129 | B2 | 4/2007 | Jackson et al. |
| 7,381,825 | B2 | 6/2008 | Bressi |
| 7,713,991 | B2 | 5/2010 | Firooznia |
| 2005/0176753 | A1 | 8/2005 | Bilodeau et al. |
| 2005/0272756 | A1 | 12/2005 | Leblanc et al. |
| 2007/0270420 | A1 | 11/2007 | Harbeson et al. |
| 2009/0018124 | A1 | 1/2009 | Kim et al. |
| 2009/0221591 | A1 | 9/2009 | Hartmann et al. |
| 2010/0261698 | A1 | 10/2010 | Adams et al. |
| 2010/0292225 | A1 | 11/2010 | Chamoin et al. |

FOREIGN PATENT DOCUMENTS

| | | |
|---|---|---|
| EP | 1389618 A1 | 2/2004 |
| JP | 2001139575 | 5/2001 |

(Continued)

OTHER PUBLICATIONS

Nath et al. (European Jounal of Organic Chemistry (1998), 10, pp. 2083-2088).*

(Continued)

*Primary Examiner* — Susanna Moore
(74) *Attorney, Agent, or Firm* — Janet E. Fair; Anna L. Cocuzzo

(57) ABSTRACT

This invention relates to pyrazolopyridyl compounds of the structural formula:

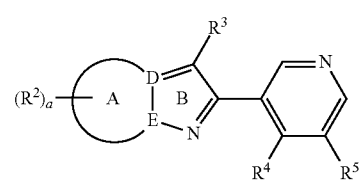

or their pharmaceutically acceptable salts, wherein the variable are defined herein. The inventive compounds selectively inhibit aldosterone synthase. This invention also provides for pharmaceutical compositions comprising the compounds of Formula I or their salts as well as potentially to methods for the treatment, amelioration or prevention of conditions that could be treated by inhibiting aldosterone synthase.

5 Claims, No Drawings

(56) References Cited

FOREIGN PATENT DOCUMENTS

| | | | |
|---|---|---|---|
| JP | 2001139575 A | | 5/2001 |
| WO | WO99/40094 A1 | | 8/1999 |
| WO | WO02/46168 A1 | | 6/2002 |
| WO | 03035065 A1 | | 5/2003 |
| WO | WO03050120 A1 | | 6/2003 |
| WO | WO03066629 | | 8/2003 |
| WO | WO2004082638 | | 9/2004 |
| WO | WO2006080821 A1 | | 8/2006 |
| WO | WO2006092430 | | 9/2006 |
| WO | WO2008/073451 A3 | | 6/2008 |
| WO | WO2009/135651 A1 | | 11/2009 |
| WO | WO2009156462 A2 | | 12/2009 |
| WO | WO2010/130796 A1 | | 11/2010 |
| WO | WO2011/061168 A1 | | 5/2011 |
| WO | WO2011/088188 A1 | | 7/2011 |
| WO | WO2012/012478 A1 | | 1/2012 |
| WO | WO2012/1148808 A1 | | 11/2012 |
| WO | WO2013/043520 A1 | | 3/2013 |
| WO | WO2013/043521 A1 | | 3/2013 |
| WO | WO2013/151876 A1 | | 10/2013 |

OTHER PUBLICATIONS

CAS Registry, Pyrazolo[1,5-a]pyridine, 3-bromo-2-(3-pyridinyl)-, SciFinder, 2001, p. 1-3.

Mahendra, Nath, et al; "An Expeditious Synthesis of Heteroarenes through Carbanion-Induced Ring Transformation Reactions of Suitable Functionalized Pyran-2-ones", European Journal of Organic Chemistry, vol. 1998, No. 10, pp. 2083-2088.

Pubchem, SCHEMBL5208366, U.S. National Library of Medicine, 2007, p. 1-12.

International Search Report for PCT/US12/55694 (Sep. 17, 2012), mailed on Jan. 29, 2013; 3 pages.

Written Opinion of the International Searching Authority for PCT/US12/55694 (Sep. 17, 2012), completed on Jan. 15, 2013; 3 pages.

Gilbert, K.C., et. al., Curr. Opin. Endocrinol. Diabetes Obes., vol. 17, 2010, pp. 199-204.

Pitt, B., et. al., New Engl. J. Med., vol. 341, 1999, pp. 709-717.

Pitt, B., et. al., New Engl. J. Med., vol. 348, 2003, pp. 1382-1390.

MacFadyen, R.J., et. al., Cardiovasc. Res., vol. 35, 1997, pp. 30-34.

Soberman, J.E., et. al., Curr. Hypertens. Rep., vol. 2, 2000, pp. 451-456.

Kawamoto, T., et. al., Proc. Natl. Acad. Sci, vol. 89, 1992, pp. 1458-1462.

Taymans, S.E., et. al., J.Clin.Endocrinol. Metab., vol. 83, 1998, pp. 1033-1036).

Lucas, et. al., J. Med. Chem., 2008, vol. 51, pp. 8077-8087.

International Search Report for PCT/US12/55697 (Sep. 17, 2012), mailed on Jan. 29, 2013; 3 pages.

Written Opinion of the International Searching Authority for PCT/US12/55697 (Sep. 17, 2012), completed on Jan. 15, 2013; 3 pages.

International Search Report for PCT/US12/55699 (Sep. 17, 2012), mailed on Feb. 5, 2013; 3 pages.

Written Opinion of the International Searching Authority for PCT/US12/55699 (Sep. 17, 2012), completed on Jan. 15, 2013; 3 pages.

* cited by examiner

PYRAZOLOPYRIDYL COMPOUNDS AS ALDOSTERONE SYNTHASE INHIBITORS

RELATED APPLICATIONS

This application claims benefit to provisional application U.S. Ser. No. 61/537,928, filed on 22 Sep. 2011, herein incorporated by reference.

FIELD OF THE INVENTION

The present invention relates to pyrazolopyridyl compounds, which selectively inhibit aldosterone synthase (CYP11B2) with diminished inhibition or affect on steroid-11-β-hydroxylase (CYP11B1) inhibitors. The inventive compounds potentially have utility in treating cardiovascular diseases such as hypertension or heart failure. The present invention also relates to pharmaceutical compositions comprising the inventive compounds as well as processes for their preparation.

BACKGROUND OF THE INVENTION

Aldosterone is a steroid hormone secreted in the adrenal cortex. In primary cells of the distal tubules and collecting ducts of the kidney, aldosterone binding to the mineralocorticoid receptor (MR) results in the retention of sodium and water and excretion of potassium, which in turn leads to increased blood pressure. Aldosterone also causes inflammation that leads to fibrosis and remodeling in the heart, vasculature and kidney. This inflammation may proceed by MR-dependent as well as MR-independent mechanisms (Gilbert, K. C. et al., Curr. Opin. Endocrinol. Diabetes Obes., vol. 17, 2010, pp. 199-204).

Mineralocorticoid receptor antagonists (MRAs), such as spironolactone and eplerenone, have been used previously to block the effects of aldosterone binding to MR. When given in addition to standard therapies such as angiotensin-converting enzyme (ACE) inhibitors and loop diuretics, the nonselective MRA spironolactone and the selective MRA eplerenone significantly reduced morbidity and mortality in patients with heart failure or myocardial infarction (Pitt, B. et al., New Engl. J. Med., vol. 341, 1999, pp. 709-717; Pitt, B. et al., New Engl. J. Med., vol. 348, 2003, pp. 1382-1390). However, the nonselective MRA spironolactone can also bind to and act at other steroid receptors, and as a consequence its use is associated with sexual side effects such as gynecomastia, dysmenorrhoea and impotence (Pitt, B. et al., New Engl. J. Med., vol. 341, 1999, pp. 709-717; MacFadyen, R. J. et al., Cardiovasc. Res., vol. 35, 1997, pp 30-34; Soberman, J. E. et al., Curr. Hypertens. Rep., vol. 2, 2000, pp 451-456). Additionally, both spironolactone and eplerenone are known to cause elevated plasma potassium levels (hyperkalemia) and elevated aldosterone levels.

An alternative method of blocking the effects of aldosterone is to inhibit its biosynthesis. CYP11B2 is a mitochondrial cytochrome P450 enzyme that catalyzes the final oxidative steps in the conversion of 11-deoxycorticosterone, a steroidal precursor, to aldosterone (Kawamoto, T. et al., Proc. Natl. Acad. Sci. USA, vol. 89, 1992, pp. 1458-1462). Compounds that inhibit CYP11B2 should thus inhibit the formation of aldosterone. Such compounds, particularly those of nonsteroidal structure, should provide the beneficial effects of MRAs, without the adverse effects derived from steroid receptor binding or MR-independent inflammatory pathways. The art has recognized that reducing aldosterone levels by inhibiting aldosterone synthase could represent a new pharmaceutical strategy that might be useful in treating a disorder or disease characterized by increased stress hormone levels and/or decreased androgen hormone levels in a patient (WO2011/088188 to Novartis). Compounds possessing this activity might be expected to treat disease states such as heart failure, cachexia, acute coronary syndrome, Cushing's syndrome or metabolic syndrome.

CYP11B1 is a related enzyme that catalyzes the formation of glucocorticoids, such as cortisol, an important regulator of glucose metabolism. Because human CYP11B2 and CYP11B1 are greater than 93% homologous, it is possible for nonselective compounds to inhibit both enzymes (Kawamoto, T. et al., Proc. Natl. Acad. Sci. USA, vol. 89, 1992, pp 1458-1462; Taymans, S. E. et al., J. Clin. Endocrinol. Metab., vol. 83, 1998, pp 1033-1036). It would be preferable, however, for therapeutic agents to selectively inhibit CYP11B2 and the formation of aldosterone with diminished inhibition of, or affect on, CYP11B1 and the production of cortisol.

WO 2009/135651 to Elexopharm describes 6-pyridin-3yl-3,4,-dihydro-1H-quinolin-2-one derivatives as being CYP11B2 inhibitors. Two compounds described therein are lactam derivatives of the formula:

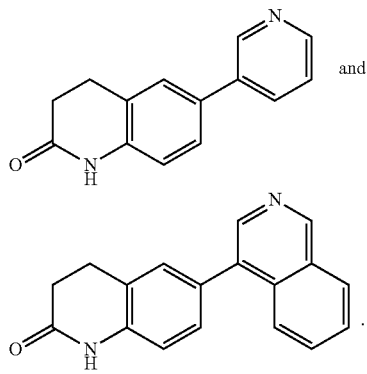

and

Structurally similar lactam and thiolactam compounds are disclosed by Lucas et al., J. Med. Chem. 2008, 51, 8077-8087; those compounds are said to be potential inhibitors of CYP11B2. Lucas et al. in J. Med. Chem. 2011, 54, 2307-2309 describes certain pyridine substituted 3,4-dihydro-1H-quinolin-2-ones as being highly potent as selective inhibitors of CYP11B2. An abstract of a dissertation reports that a series of novel heterocyclic-substituted 4,5-dihydro-[1,2,4]triazolo[4,3a]quinolones was evaluated for its aldosterone synthase activity; one of the compounds is reported as exhibiting excellent selectivity of CYP11B2 over CYP11B1.

Benzimidazole derivatives are also known in the art to treat various disease states. For example, U.S. Pat. No. 6,897,208 to Aventis Pharmaceuticals describes compounds of the formula:

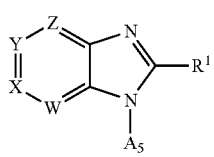

wherein $R^1$ is an optionally substituted aryl or heteroaryl group and $A_5$ is H or alkyl. These compounds are said to be kinase inhibitors. Other benzimidazoles derivatives are known in the art. For example, WO 2012/012478 to Merck describes benzimidazole analogues as having the ability to CYP11B2. WO2002/46168 A1 to AstraZeneca describes benzimidazoles derivatives that are useful in the treatment or prophylaxis of Alzheimer's disease, anxiety disorders, depressive disorders, osteoporosis, cardiovascular disease, rheumatoid arthritis or prostate cancer. US2007/0270420 A1 to Vertex Pharmaceuticals describes benzimidazole compounds that are useful of inhibitors of GSK-3 and Lck protein kineases. Other benzimidazole derivatives are described in US 2009/0018124 A1, WO2004/082638 A1, WO2008/073451 A1 and US 2005/0272756 A1.

Novartis in US 2010/0261698 A1 describes indole derivatives of the formula:

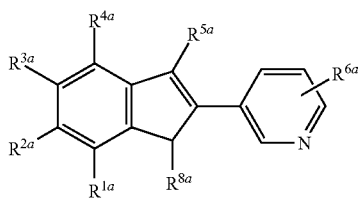

Novartis indicates that these compounds inhibit aldosterone synthase and may be useful in the treatment of disease states such as heat failure and hypertension. In WO2010/130,796 A1 and WO2011/061168, Novartis discloses aryl-pyridine derivatives that are said to inhibit aldosterone synthase.

US 2009/0221591 A1 to Universitat des Saarlandes also discloses compounds that inhibit CYP11B1 and CYP11B2. WO 2009/135651 to Universitat des Saarlandes teaches that compounds of the formula:

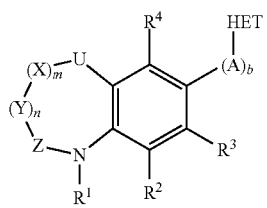

possess the ability to inhibit aldosterone synthase.

WO 1999/400094 Bayer AG discloses oxazolidinones with azol-containing tricycles as having antibacterial activity.

U.S. Pat. No. 7,381,825 to Takeda describes histone deacetylase inhibitors of the formula

Z-Q-L-M where Q is a substituted or unsubstituted aromatic ring, L is a substituent providing between 0-10 atoms separation between M and the remainder of the compound, M is a substituent capable of complexing with a deacetylase catalytic site and/or metal ion, and Z is list of bicyclic groups, including, but not limited to:

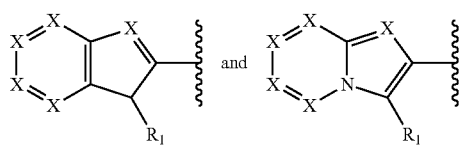

where X is $CR_{12}$ or N. These compounds are said to be useful in treating cell-proliferative diseases such as, for example, leukemia, melanoma, bladder cancer, etc.

SUMMARY OF THE INVENTION

In its many embodiments, the present invention provides for novel pyrazolopyridyl compounds, which are inhibitors of CYP11B2, or metabolites, stereoisomers, salts, solvates or polymorphs thereof, processes of preparing such compounds, pharmaceutical compositions comprising one or more such compounds, processes of preparing pharmaceutical compositions comprising one or more such compounds and potentially methods of treatment, inhibition or amelioration of one or more disease states associated with inhibiting CYP11B2 by administering an effective amount at least one of the inventive pyrazolopyridyl compounds to a patient in need thereof.

In one aspect, the present application discloses a compound or a pharmaceutically acceptable salt, metabolite, solvate, prodrug or polymorph of said compound, said compound having the general structure shown in Formula I

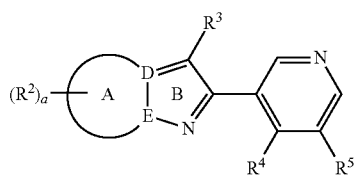

I wherein:
Ring A is attached to Ring B via positions D and E and is:

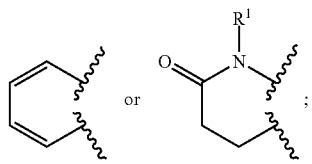

D is C;
E is N;
$R^1$ is H or alkyl;
$R^2$ is halogen; —CN; —$OR^7$; —$N(R^{10})C(O)R^7$; —$NR^{11}R^{12}$; —$C(O)R^7$; —$C(O)N(R^{11})(R^{12})$; —$C(O)OR^7$; —$SO_2N(R^{10})$—$R^7$; —$N(R^{10})SO_2$—$R^7$; —$S(O)_m$—$R^7$; alkyl optionally substituted one or more times (e.g., 1 to 4 times) by halogen, —$OR^7$, $NR^8R^9$, —CN, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; cycloalkyl optionally substituted one or more times (e.g., 1 to 4 times) by halogen, alkyl, haloalkyl, —$OR^7$, —$NR^8R^9$, —CN, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; heterocycloalkyl optionally substituted one or more times (e.g., 1 to 4 times) by halogen, alkyl, haloalkyl, —$OR^7$, —CN, —$NR^8R^9$—$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; aryl optionally substituted one or more times (e.g., 1 to 4 times) by halogen, alkyl, haloalkyl, cycloalkyl, —$OR^7$, —CN, —$NR^8R^9$—$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; or heteroaryl optionally substituted one or more times (e.g., 1 to 4 times) by halogen, alkyl, haloalkyl, cycloalkyl, —$OR^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^3$ is H; halogen; —CN; alkyl optionally substituted one or more times (e.g., 1 to 4 times) by halogen or cycloalkyl optionally substituted once or twice by alkyl or halogen; cycloalkyl optionally substituted once or twice by alkyl or halogen; aryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)(R$^7$), —C(O)N(R$^8$)(R$^9$), —C(O)OR$^7$—SO$_2$N(R$^{10}$)—R$^7$, —N(R$^{10}$)SO$_2$—R$^7$, or —S(O)$_m$—R$^7$; or —C(O)OR$^7$;

R$^4$ is H; halogen; —CN; —OR$^7$; —NR$^8$R$^9$; —N(R$^{10}$)C(O)R$^7$; —C(O)N(R$^8$)(R$^9$); —C(O)R$^7$; —C(O)OR$^7$; —SO$_2$N(R$^{10}$)—R$^7$; —N(R$^{10}$)S(O)$_2$—R$^7$; —S(O)$_n$—R$^7$; alkyl optionally substituted one or more times (e.g., 1 to 4 times) by halogen, —OR$^7$, —NR$^8$R$^9$, —CN, —N(R$^{11}$)C(O)R$^7$, —C(O)N(R$^8$)(R$^9$), —C(O)OR$^7$, —SO$_2$N(R$^{10}$)—R$^7$, —N(R$^{10}$)S(O)$_2$—R$^7$, or —S(O)$_n$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^8$, —SO$_2$N(R$^{10}$)—R$^7$, —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)(R$^7$), —C(O)N(R$^8$)(R$^9$), —C(O)OR$^7$—SO$_2$N(R$^{10}$)—R$^7$, —N(R$^{10}$)SO$_2$—R$^7$, or —S(O)$_m$—R$^7$; heterocycloalkyl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$—SO$_2$N(R$^{10}$)—R$^7$, —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^5$ is H; halogen; —CN; —OR$^7$; —NR$^8$R$^9$; —N(R$^{10}$)C(O)R$^7$; —C(O)N(R$^8$)(R$^9$); —C(O)R$^7$; —C(O)OR$^7$; —SO$_2$N(R$^{10}$)—R$^7$; —N(R$^{10}$)S(O)$_2$—R$^7$; —S(O)$_n$—R$^7$; alkyl optionally substituted one or more times (e.g., 1 to 4 times) by halogen, —OR$^7$, —NR$^8$R$^9$, —CN, —N(R$^{11}$)C(O)R$^7$, —C(O)N(R$^8$)(R$^9$), —C(O)OR$^7$, —SO$_2$N(R$^{10}$)—R$^7$, —N(R$^{10}$)S(O)$_2$—R$^7$, or —S(O)$_n$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

or R$^4$ and R$^5$ are joined together to form a 5-7 membered carbocyclic or heterocyclic ring that is fused to the pyridyl ring to which R$^4$ and R$^5$ are attached, wherein the ring formed by R$^4$ and R$^5$ is optionally substituted by 1 to 3 R$^6$;

R$^6$ is independently H; halogen; —CN; —OR$^7$; —NR$^8$R$^9$; —N(R$^{10}$)C(O)R$^7$; —C(O)N(R$^7$)(R$^8$); —C(O)N(R$^8$)(R$^9$); —C(O)OR$^7$; —SO$_2$N(R$^{10}$)—R$^7$; —N(R$^{10}$)SO$_2$—R$^7$; —S(O)$_m$—R$^7$; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$—SO$_2$N(R$^{10}$)—R$^7$, —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^7$ is independently H; alkyl optionally substituted one or more times (e.g., 1 to 4 times) by halogen, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; cycloalkyl optionally substituted one or more times (e.g., 1 to 4 times) by halogen, alkyl, haloalkyl, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; aryl optionally substituted one or more times (e.g., 1 to 4 times) by halogen, alkyl, haloalkyl, cycloalkyl, —OH, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; or heteroaryl optionally substituted one or more times (e.g., 1 to 4 times) by halogen, alkyl, haloalkyl, cycloalkyl, —OR$^{10}$, —NR$^8$R$^9$, —CN, —N(R$^9$)C(O)R$^{10}$, —C(O)N(R$^8$)(R$^9$), —C(O)OR$^{10}$ or —S(O)$_m$—R$^{10}$;

R$^8$ is independently H or alkyl;

R$^9$ is independently H or alkyl;

or R$^8$ and R$^9$ are joined together with the nitrogen to which they are attached form a saturated 5- to 7-membered heterocyclic ring;

R$^{10}$ is independently H or alkyl;

R$^{11}$ is independently H; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

R$^{12}$ is independently H; alkyl optionally substituted one or more times (e.g., 1 to 4 times) by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$ or —S(O)$_m$—R$^7$; or heteroaryl optionally substituted one or more times (e.g., 1 to 4 times) by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

a is 0, 1, 2, 3 or 4 (e.g., 0, 1, or 2);
n is 1 or 2; and
m is 0, 1 or 2.

Another aspect of the present invention is pharmaceutical compositions comprising a therapeutically effective amount of at least one compound of Formula I or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, a therapeutically effective amount of at least one additional therapeutic agent and a pharmaceutically acceptable carrier.

Another aspect of the present invention is the prevention of one or more disease states associated with inhibiting CYP11B2 by administering an effective amount of at least one of the inventive pyrazolopyridyl compounds to a patient in need thereof.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a therapeutic agent.

The compounds of the present invention could be useful in the treatment, amelioration or prevention of one or more conditions associated with inhibiting CYP11B2 by administering a therapeutically effective amount of at least one compound of Formula I or a pharmaceutically acceptable salt thereof to a mammal in need of such treatment. Conditions that could be treated or prevented by inhibiting CYP 11B2 include hypertension, heart failure such as congestive heart failure, diastolic dysfunction, left ventricular diastolic dysfunction, heart failure (including congestive heart failure), diastolic dysfunction, left ventricular diastolic dysfunction, diastolic heart failure, systolic dysfunction, hypokalemia, renal failure (including chronic renal failure), restenosis, syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, ischemia, myocardial and vascular fibrosis, myocardial necrotic lesions, vascular damage, myocardial necrotic lesions, vascular damage, myocardial infarction, left ventricular hypertrophy, cardiac lesions, vascular wall hypertrophy, endothelial thickening or fibrinoid necrosis of coronary arteries.

The compounds of the present invention also might be useful in treating one or more conditions characterized by increased stress hormone levels and/or decreased androgen hormone levels in a mammal by administering a therapeutically effective amount of at least one compound of Formula I or a pharmaceutically acceptable salt thereof to a mammal in need of such treatment. Conditions characterized by increased stress hormone levels and/or decreased androgen hormone levels in a mammal include, for example, heart failure (e.g., acute heart failure, acute decompensated heart failure, chronic heart failure, chronic heart failure with impaired exercise tolerance or chromic heart failure with muscle weakness), cachexia (e.g., cardiac cachexia, COPD-induced cachexia, cirrhosis-induced cachexia, tumor-induced cachexia or viral (HIV)-induced cachexia), acute coronary syndrome, Cushing's syndrome or metabolic syndrome.

Another aspect of the present invention could be the possible use of a compound of Formula I or a pharmaceutically acceptable salt thereof for the manufacture of a medicament for the treatment, amelioration or prevention of one or more conditions associated with inhibiting CYP11B2 in a patient.

This invention further relates to process for the preparation of the compounds of Formula I or their pharmaceutically acceptable salts. Moreover, this invention also relates to the use of the compounds of Formula I or their pharmaceutically acceptable salts to validate in vitro assays, such as, for example the V79-Human-CYP11B2 and V79-Human-CYP11B1 discussed later in the application.

These and other objectives will be evident from the description of the invention contained herein.

DETAILED DESCRIPTION

In an embodiment, the present invention provides compounds represented by structural Formula I or pharmaceutically acceptable salt thereof, wherein the various moieties are as described as above.

Another embodiment of the present invention is compounds or their pharmaceutically acceptable salts of Formula I wherein:

Ring A is attached to Ring B via positions D and E and is:

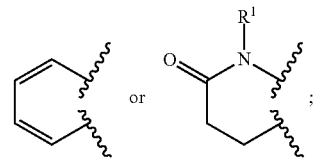

D is C;
E is N;
R$^1$ is H or alkyl;
R$^2$ is halogen; —CN; —OR$^7$; —N(R$^{10}$)C(O)R$^7$; —NR$^{11}$R$^{12}$; —C(O)R$^7$, —C(O)N(R$^{11}$)(R$^{12}$); —C(O)OR$^7$; —SO$_2$N(R$^{10}$)—R$^7$; —N(R$^{10}$)SO$_2$—R$^7$; —S(O)$_m$—R$^7$; alkyl optionally substituted one or more times (e.g., 1 to 4 times) by halogen, —OR$^7$, NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; cycloalkyl optionally substituted one or more times (e.g., 1 to 4 times) by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times (e.g., 1 to 4 times) by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times (e.g., 1 to 4 times) by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N ($R^{10}$)—$R^7$, —N($R^{10}$)$SO_2$—$R^7$ or —S(O)$_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$;

$R^3$ is H; halogen; —CN; alkyl optionally substituted one or more times (e.g., 1 to 4 times) by halogen or cycloalkyl optionally substituted once or twice by alkyl or halogen; cycloalkyl optionally substituted once or twice by alkyl or halogen; or —C(O)$OR^7$;

$R^4$ is H; halogen; —CN; —$OR^7$; —$NR^8R^9$; —N($R^{10}$)C(O)$R^7$; —C(O)N($R^8$)($R^9$); —C(O)$R^7$; —C(O)$OR^7$; —$SO_2$N($R^{10}$)—$R^7$; —N($R^{10}$)S(O)$_2$—$R^7$; —S(O)$_o$—$R^7$; alkyl optionally substituted one or more times (e.g., 1 to 4 times) by halogen, —$OR^7$, —$NR^8R^9$, —CN, —N($R^{11}$)C(O)$R^7$, —C(O)N($R^8$)($R^9$), —C(O)$OR^7$, —$SO_2$N($R^{10}$)—$R^7$, —N($R^{10}$)S(O)$_2$—$R^7$, or —S(O)$_n$—$R^7$; cycloalkyl optionally substituted one or more times (e.g., 1 to 4 times) by halogen, alkyl, haloalkyl, —$OR^7$, —$NR^8R^9$, —CN, —N($R^{10}$)C(O)$R^7$, —C(O)N($R^8$)($R^9$), —C(O)$OR^8$, —$SO_2$N($R^{10}$)—$R^7$, —N($R^{10}$)$SO_2$—$R^7$ or —S(O)$_m$—$R^7$; aryl optionally substituted one or more times (e.g., 1 to 4 times) by halogen, alkyl, haloalkyl, cycloalkyl, —$OR^7$, —CN, —$NR^8R^9$, —N($R^{10}$)C(O)($R^7$), —C(O)N($R^8$)($R^9$), —C(O)$OR^7$—$SO_2$N($R^{10}$)—$R^7$, —N($R^{10}$)$SO_2$—$R^7$, or —S(O)$_m$—$R^7$; heterocycloalkyl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$—$SO_2$N($R^{10}$)—$R^7$, —N($R^{10}$)$SO_2$—$R^7$ or —S(O)$_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$;

$R^5$ is H; halogen; —CN; —$OR^7$; —$NR^8R^9$; —N($R^{10}$)C(O)$R^7$; —C(O)N($R^8$)($R^9$); —C(O)$R^7$; —C(O)$OR^7$; —$SO_2$N($R^{10}$)—$R^7$; —N($R^{10}$)S(O)$_2$—$R^7$; —S(O)$_n$—$R^7$; alkyl optionally substituted one or more times (e.g., 1 to 4 times) by halogen, —$OR^7$, —$NR^8R^9$, —CN, —N($R^{11}$)C(O)$R^7$, —C(O)N($R^8$)($R^9$), —C(O)$OR^7$, —$SO_2$N($R^{10}$)—$R^7$, —N($R^{10}$)S(O)$_2$—$R^7$, or —S(O)$_n$—$R^7$; cycloalkyl optionally substituted one or more times (e.g., 1 to 4 times) by halogen, alkyl, haloalkyl, —$OR^7$, —$NR^8R^9$, —CN, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$; aryl optionally substituted one or more times (e.g., 1 to 4 times) by halogen, alkyl, haloalkyl, cycloalkyl, —$OR^7$, —CN, —$NR^8R^9$—N($R^{10}$)C(O)($R^7$), —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$; heterocycloalkyl optionally substituted one or more times (e.g., 1 to 4 times) by halogen, alkyl, haloalkyl, cycloalkyl, —$OR^7$, —CN, —$NR^8R^9$—N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$;

or $R^4$ and $R^5$ are joined together to form a 5-7 membered carbocyclic or heterocyclic ring that is fused to the pyridyl ring to which $R^4$ and $R^5$ are attached, wherein the ring formed by $R^4$ and $R^5$ is optionally substituted by 1 to 3 $R^6$;

$R^6$ is independently H; halogen; —CN; —$OR^7$; —$NR^8R^9$; —N($R^{10}$)C(O)$R^7$; —C(O)N($R^7$)($R^8$); —C(O)N($R^8$)($R^9$); —C(O)$OR^7$; —$SO_2$N($R^{10}$)—$R^7$; —N($R^{10}$)$SO_2$—$R^7$; —S(O)$_m$—$R^7$; alkyl optionally substituted one or more times (e.g., 1 to 4 times) by halogen, —$OR^7$, —$NR^8R^9$, —CN, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$; cycloalkyl optionally substituted one or more times (e.g., 1 to 4 times) by halogen, alkyl, haloalkyl, —$OR^7$, —$NR^8R^9$, —CN, —N($R^{10}$)C(O)$R^7$, —C(O)N($R^8$)($R^9$), —C(O)$OR^7$—$SO_2$N($R^{10}$)—$R^7$, —N($R^{10}$)$SO_2$—$R^7$ or —S(O)$_m$—$R^7$; aryl optionally substituted one or more times (e.g., 1 to 4 times) by halogen, alkyl, haloalkyl, cycloalkyl, —$OR^7$, —CN, —$NR^8R^9$—N($R^{10}$)C(O)($R^7$), —C(O)N($R^7$)($R^8$), —C(O)$OR^7$, —$SO_2$N($R^{10}$)—$R^7$, —N($R^{10}$)$SO_2$—$R^7$ or —S(O)$_m$—$R^7$; heterocycloalkyl optionally substituted one or more times (e.g., 1 to 4 times) by halogen, alkyl, haloalkyl, —$OR^7$, —CN, —$NR^8R^9$—N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$, —$SO_2$N($R^{10}$)—$R^7$, —N($R^{10}$)$SO_2$—$R^7$ or —S(O)$_m$—$R^7$;

$R^7$ is independently H; alkyl optionally substituted one or more times (e.g., 1 to 4 times) by halogen, —$OR^{10}$, —$NR^8R^9$, —CN, —N($R^{10}$)C(O)$R^{10}$, —C(O)N($R^8$)($R^9$), —C(O)$OR^{10}$ or —S(O)$_m$—$R^{10}$; cycloalkyl optionally substituted one or more times (e.g., 1 to 4 times) by halogen, alkyl, haloalkyl, —$OR^{10}$, —$NR^8R^9$, —CN, —N($R^{10}$)C(O)$R^{10}$, —C(O)N($R^8$)($R^9$), —C(O)$OR^{10}$ or —S(O)$_m$—$R^{10}$; aryl optionally substituted one or more times (e.g., 1 to 4 times) by halogen, alkyl, haloalkyl, cycloalkyl, —OH, —$OR^{10}$, —$NR^8R^9$, —CN, —N($R^{10}$)C(O)$R^{10}$, —C(O)N($R^8$)($R^9$), —C(O)$OR^{10}$ or —S(O)$_m$—$R^{10}$; or heteroaryl optionally substituted one or more times (e.g., 1 to 4 times) by halogen, alkyl, haloalkyl, cycloalkyl, —$OR^{10}$, —$NR^8R^9$, —CN, —N($R^9$)C(O)$R^{10}$, —C(O)N($R^8$)($R^9$), —C(O)$OR^{10}$ or —S(O)$_m$—$R^{10}$;

$R^8$ is independently H or alkyl;

$R^9$ is independently H or alkyl;

or $R^8$ and $R^9$ are joined together with the nitrogen to which they are attached form a saturated 5- to 7-membered heterocyclic ring;

$R^{10}$ is independently H or alkyl;

$R^{11}$ is independently H; alkyl optionally substituted one or more times (e.g., 1 to 4 times) by halogen, —$OR^7$, —$NR^8R^9$, —CN, —N($R^{10}$)C(O)$R^7$, —C(O)N($R^8$)($R^9$), —C(O)$OR^7$ or —S(O)$_m$—$R^7$; cycloalkyl optionally substituted one or more times (e.g., 1 to 4 times) by halogen, alkyl, haloalkyl, —$OR^7$, —$NR^8R^9$, —CN, —N($R^{10}$)C(O)$R^7$, —C(O)N($R^8$)($R^9$), —C(O)$OR^{10}$ or —S(O)$_m$—$R^{10}$; aryl optionally substituted one or more times (e.g., 1 to 4 times) by halogen, alkyl, haloalkyl, cycloalkyl, —$OR^7$, —CN, —$NR^8R^9$—N($R^{10}$)C(O)($R^7$), —C(O)N($R^7$)($R^8$), —C(O)$OR^7$ or —S(O)$_m$—$R^7$; heterocycloalkyl optionally substituted one or more times (e.g., 1 to 4 times) by halogen, alkyl, haloalkyl, —$OR^7$, —CN, —$NR^8R^9$—N($R^{10}$)C(O)$R^7$, —C(O)N($R^8$)($R^9$), —C(O)$OR^7$ or —S(O)$_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —N($R^{10}$)C(O)$R^7$, —C(O)N($R^8$)($R^9$), —C(O)$OR^7$ or —S(O)$_m$—$R^7$;

$R^{12}$ is independently H; alkyl optionally substituted one or more times (e.g., 1 to 4 times) by halogen, —$OR^7$, —$NR^8R^9$, —CN, —N($R^{10}$)C(O)$R^7$, —C(O)N($R^8$)($R^9$), —C(O)$OR^7$ or —S(O)$_m$—$R^7$; cycloalkyl optionally substituted one or more times (e.g., 1 to 4 times) by halogen, alkyl, haloalkyl, —$OR^7$, —$NR^8R^9$, —CN, —N($R^{10}$)C(O)$R^7$, —C(O)N($R^8$)($R^9$), —C(O)$OR^{10}$ or —S(O)$_m$—$R^{10}$; aryl optionally substituted one or more times (e.g., 1 to 4 times) by halogen, alkyl, haloalkyl, cycloalkyl, —OR⁷, —CN, —NR⁸R⁹—N(R¹⁰)C(O)(R⁷), —C(O)N(R⁷)(R⁸), —C(O)OR⁷ or —S(O)ₘ—R⁷; heterocycloalkyl optionally substituted one or more times (e.g., 1 to 4 times) by halogen, alkyl, haloalkyl, —OR⁷, —CN, —NR⁸R⁹—N(R¹⁰)C(O)R⁷, —C(O)N(R⁸)(R⁹), —C(O)OR⁷ or —S(O)ₘ—R⁷; or heteroaryl optionally substituted one or more times (e.g., 1 to 4 times) by halogen, alkyl, haloalkyl, cycloalkyl, —OR⁷, —CN, —NR⁸R⁹, —N(R¹⁰)C(O)R⁷, —C(O)N(R⁸)(R⁹), —C(O)OR⁷ or —S(O)ₘ—R⁷;

a is 0, 1, 2, 3 or 4 (e.g., 0, 1, or 2);

n is 1 or 2; and m is 0, 1 or 2.

Another embodiment of the present invention is compounds or their pharmaceutically acceptable salts of Formula I represented by structural Formula II

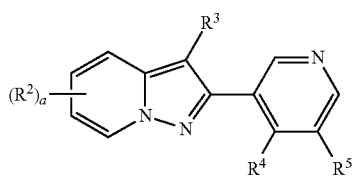

II wherein R², R³, R⁴, R⁵ and a are as defined in Formula I.

Another embodiment of the present invention is compounds or their pharmaceutically acceptable salts of Formula I represented by structural Formula III

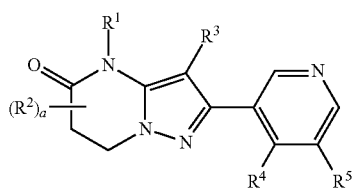

III wherein R¹, R², R³, R⁴, R⁵ and a are as defined in Formula I.

Another embodiment of the present invention is compounds or their pharmaceutically acceptable salts of Formula I represented by structural Formula IV

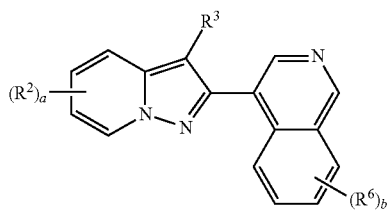

IV wherein R², R³, R⁶ and a are as defined in Formula I and b is 0, 1 or 2 (e.g, where b is 0, or where b is 1 or 2 and R⁶ is alkyl or halo).

Another embodiment of the present invention is compounds or their pharmaceutically acceptable salts of Formula I represented by structural Formula V

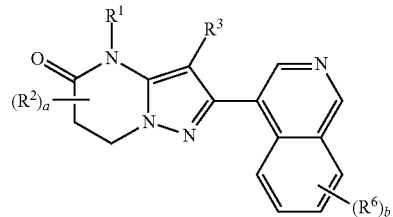

V wherein R¹, R², R³, R⁶ and a are as defined in Formula I and b is 0, 1 or 2 (e.g, where b is 0, or where b is 1 or 2 and R⁶ is alkyl or halo).

Another embodiment of the present invention is compounds or their pharmaceutically acceptable salts of any of the embodiments of Formulae I through V, a is 0 or a is 1 or 2 and R² is independently halogen (e.g., F or Cl), —CN, alkyl (e.g., methyl, ethyl, n-propyl, i-propyl, n-butyl, iso-butyl, sec-butyl, tert-butyl), OR⁷ (where R⁷ is H, alkyl (e.g., methyl, ethyl, n-propyl, i-propyl, n-butyl, iso-butyl, sec-butyl, tert-butyl) or haloalkyl (e.g., —CF₃)), haloalkyl (e.g., —CF₃), cycloalkyl (e.g., cyclopropyl or cyclohexyl) or phenyl optionally substituted by halogen.

Another embodiment of the present invention is compounds or their pharmaceutically acceptable salts of any the embodiments of Formulae I through V described above where R³ is H, halogen, —CN, alkyl (e.g., methyl, ethyl, n-propyl, i-propyl, n-butyl, iso-butyl, sec-butyl, tert-butyl), or cycloalkyl (e.g., cyclopropyl or cyclohexyl).

Another embodiment of the present invention is compounds or their pharmaceutically acceptable salts of any of the embodiments of formulae I through V described above where R³ is phenyl which is optionally substitute once or twice by alkyl, halogen or haloalkyl.

Another embodiment of the present invention is compounds or their pharmaceutically acceptable salts of any of the embodiments of Formulae I through III above where R⁴ is H, halogen (e.g., —F or —Cl), —CN, alkyl (e.g., methyl or ethyl) or cycloalkyl (e.g., cyclopropyl, cyclobutyl, cyclopentyl or cyclohexyl).

Another embodiment of the present invention is compounds or their pharmaceutically acceptable salts of any of the embodiments of Formulae I through III above where R⁴ is H or alkyl (e.g., methyl or ethyl).

Another embodiment of the present invention is compounds or their pharmaceutically acceptable salts of any of the embodiments of Formulae I through III above where R⁵ is H, halogen (e.g., —F or —Cl), —CN, alkyl (e.g., methyl, ethyl, n-propyl, i-propyl, n-butyl, iso-butyl, sec-butyl, tert-butyl), —OR⁷ (where R⁷ is H, alkyl (e.g., methyl, ethyl, n-propyl, i-propyl, n-butyl, iso-butyl, sec-butyl, tert-butyl), haloalkyl (e.g., —CF₃)), haloalkyl (e.g., —CF₃) or phenyl optionally substituted by halogen, —OR⁷ (where R⁷ is H, alkyl (e.g., methyl, ethyl, n-propyl, i-propyl, n-butyl, iso-butyl, sec-butyl, tert-butyl) or haloalkyl (e.g., —CF₃)) or haloalkyl (e.g., —CF₃).

Another embodiment of the present invention is compounds or their pharmaceutically acceptable salts thereof of any of the embodiments of Formula I through III wherein R⁵ is cycloalkyl (e.g., cyclopropyl).

Another embodiment of the present invention is compounds or their pharmaceutically acceptable salts thereof of any of the embodiments of Formula I through III described above where R⁴ is H and R⁵ is H, halogen (e.g., —F or —Cl), —CN, alkyl (e.g., methyl, ethyl, n-propyl, i-propyl, n-butyl, iso-butyl, sec-butyl, tert-butyl), —OR$^7$ (where R$^7$ is H, alkyl (e.g., methyl, ethyl, n-propyl, i-propyl, n-butyl, iso-butyl, sec-butyl, tert-butyl), haloalkyl (e.g., —CF$_3$)), haloalkyl (e.g., —CF$_3$) or phenyl optionally substituted by halogen, —OR$^7$ (where R$^7$ is H, alkyl (e.g., methyl, ethyl, n-propyl, i-propyl, n-butyl, iso-butyl, sec-butyl, tert-butyl) or haloalkyl (e.g., —CF$_3$)) or haloalkyl (e.g., —CF$_3$).

Another embodiment of the present invention is compounds or their pharmaceutically acceptable salts thereof of any of the embodiments of Formulae I through III described above where R$^5$ is —C(O)OR$^7$ (e.g., R$^7$ is C$_1$-C$_4$-alkyl or phenyl, optionally substituted by halogen or haloalkyl).

Another embodiment of the present inventions is compounds or their pharmaceutically acceptable salts thereof of any of the embodiments of Formula I through III described above or their pharmaceutically acceptable salts thereof where R$^4$ is H and R$^5$ is a group of the formula:

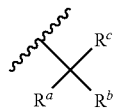

where:
R$^a$ is H, OH, or —C$_1$-C$_3$-alkyl optionally substituted with 1 to 3-F (e.g. —CF$_3$);
R$^b$ is H, —OH, or —C$_1$-C$_3$-alkyl optionally substituted with 1 to 3-F (e.g. —CF$_3$);
R$^c$ is —C$_1$-C$_3$-alkyl optionally substituted with 1 to 3-F (e.g. —CF$_3$), is —OC$_1$-C$_3$-alkyl, —N(H)S(O)$_2$—C$_1$-C$_3$-alkyl, optionally substituted with 1 to 3-F (e.g. —CF$_3$), —N(H)C(O)C$_1$-C$_3$-alkyl, optionally substituted with 1 to 3-F (e.g. —CF$_3$).

Another embodiment of the present inventions is compounds or their pharmaceutically acceptable salts thereof of any of the embodiments of Formula I through III described above or their pharmaceutically acceptable salts thereof where R$^3$ is alkyl (e.g., methyl or ethyl), cycloalkyl (e.g., cyclopropyl), or phenyl; R$^4$ is H, alkyl (e.g., methyl or ethyl), or cycloalkyl (e.g. cyclopropyl); R$^5$ is H, halogen, —OR$^7$ (where R$^7$ is H or alkyl (e.g., methyl or ethyl)); —CN; or haloalkyl (e.g., —CF$_3$).

As used above, and throughout this disclosure, the following terms, unless otherwise indicated, shall be understood to have the following meanings:

"Mammal" means humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Halo" refers to fluorine, chlorine, bromine or iodine radicals. Examples are fluoro, chloro or bromo.

"Halogen" means fluorine, chlorine, bromine, or iodine.

"Haloalkyl" means a halo-alkyl- group in which the alkyl group is as previously described. The bond to the parent moiety is through the alkyl. Non-limiting examples of suitable haloalkyl groups include fluoromethyl, difluoromethyl, —CH$_2$CF$_3$, —CH$_2$CHF$_2$—CH$_2$CH$_2$F, or an alkyl group with one or more terminal carbons tri-substituted with a halogen (e.g., —F) such as, for example —C$_1$-C$_3$alkyl-CF$_3$, —CH(CH$_3$)(CF$_3$), —CH(CF$_3$)$_2$ and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Aryl" means an aromatic monocyclic or multicyclic ring system comprising about 6 to about 14 carbon atoms, preferably about 6 to about 10 carbon atoms. Non-limiting examples of suitable aryl groups include phenyl, naphthyl, indenyl, tetrahydronaphthyl and indanyl.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist protected such as, for example, as an —N(Boc), —N(CBz), —N(Tos) group and the like; such protections are also considered part of this invention. The nitrogen or sulfur atom of the heterocycloalkyl ring can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,3-dioxanyl, 1,4-dioxanyl, tetrahydrofuranyl, tetrahydrothiopyranyl, oxetanyl, tetrahydrothiophenyl, lactam, lactone, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination, provided that the rings do not include adjacent oxygen and/or sulfur atoms. N-oxides of the ring nitrogens are also included, as well as compounds wherein a ring nitrogen is substituted by an alkyl group to form a quaternary amine. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, oxadiazolyl, tetrazolyl, pyrimidyl, furazanyl, pyrrolyl, pyrazolyl, triazolyl, 1,2,4-thiadiazolyl, pyrazinyl, pyridazinyl, quinoxalinyl, phthalazinyl, oxindolyl, naphthyridyl (e.g., 1, 5 or 1,7), pyrido[2,3]imidazolyl, imidazo[1,2-a]pyridinyl, imidazo[2,1-b]thiazolyl, benzofuranyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzoxazolyl, benzothiazolyl, pyridopyrimidinyl, 7-azaindolyl and the like. The term "heteroaryl" also refers to partially saturated heteroaryl moieties such as, for example, tetrahydroisoquinolyl, tetrahydroquinolyl and the like. All positional isomers are contemplated, e.g., 2-pyridyl, 3-pyridyl and 4-pyridyl.

It should be noted that in heterocycloalkyl ring systems of this invention, there are no hydroxyl groups on carbon atoms adjacent to a N, O or S, as well as there are no N or S groups on carbon adjacent to another heteroatom. Thus, for example, in the ring:

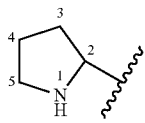

there is no —OH attached directly to carbons marked 2 and 5.

It should also be noted that tautomeric forms such as, for example, the moieties:

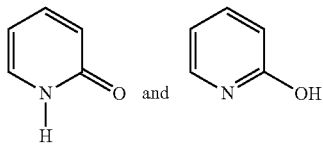 [SMILES: O=c1cccc[nH]1 ; Oc1ccccn1]

are considered equivalent in certain embodiments of this invention.

When $R^4$ and $R^5$ are joined together to form a 5-7 membered carbocyclic ring that is fused to the pyridyl ring to which $R^4$ and $R^5$ are attached, "carbocyclic" means a cycloalkyl, aryl or partially unsaturated ring composed of 5-7 carbon atoms wherein two of the carbons are shared between the fused rings. When $R^4$ and $R^5$ are joined together to form a 5-7 membered heterocyclic ring that is fused to the pyridyl ring to which $R^4$ and $R^5$ are attached, "heterocyclic" means a fully saturated, partially saturated or aromatic ring composed of carbon atoms and one, two or three heteroatoms selected from N, S, or O, wherein two of the carbons are shared between the fused rings. Representative ring include:

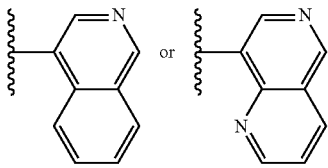

When a moiety can be optionally substituted, it means that each carbon and heteroatom (when present) available for substitution in the given moiety may be independently unsubstituted or substituted with specified number of substituents that are the same or different at each occurrence and which result in the creation of a stable structure as is understood to be reasonable by one skilled in the art.

Unless expressly depicted or described otherwise, variables depicted in a structural formula with a "floating" bond, such as $R^2$ in structural Formula III, are permitted on any available carbon atom in the ring to which each is attached.

When $R^8$ and $R^9$ together with the nitrogen to which they are attached form a saturated 5- to 7-membered heterocyclic ring, this means a saturated heterocyclic ring composed of, in addition to the one nitrogen atom, carbon atoms and optionally one additional heteroatom selected from N, S or O. Representative examples include:

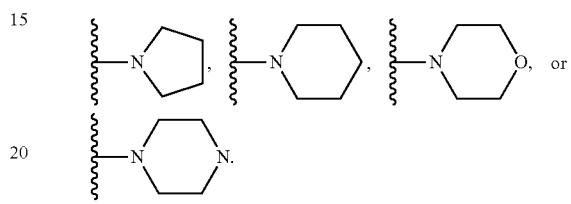

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally, a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of this invention as those of a specific formula or embodiment, e.g., Formula I (which includes the compounds of Formulae II-V) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding physiologically or toxicologically acceptable salts, in particular the pharmaceutically utilizable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Compounds of the present invention are effective at inhibiting the synthesis of aldosterone by inhibiting CYP11B2 (aldosterone synthase) and they are therefore useful agents for the therapy and prophylaxis of disorders that are associated with elevated aldosterone levels. Accordingly, an embodiment of the instant invention is to provide a method for inhibiting aldosterone synthase, and more particularly selectively inhibiting CYP11B2, in a patient in need thereof, comprising administering a compound of Formula I to the patient in an amount effective to inhibit aldosterone synthesis, or more particularly to selectively inhibit CYP11B2, in the patient. A selective inhibitor of CYP11B2 is intended to mean a compound that preferentially inhibits CYP11B2 as compared to CYP11B1. The inhibition of CYP11B2, as well inhibition of CYP11B1, by the compounds of Formula I can be examined, for example, in the inhibition assays described below.

In general, compounds that have activity as aldosterone synthase inhibitors can be identified as those compounds which have an $IC_{50}$ of less than or equal to about 10 µM; preferably less than or equal to about 250 nM; and most preferably less than or equal to about 100 nM, in the V79-Human-CYP11B2 Assay described below. In general, aldosterone synthase inhibitors that are selective for inhibition of CYP11B2 as compared to CYP11B1 are those that show at least 3-fold greater inhibition for CYP11B2 compared to CYP11B1; preferably at least 20-fold inhibition for CYP11B2 compared to CYP11B1; and more preferably at least 100-fold greater inhibition for CYP11B2 compared to CYP11B1, in the V79-Human-CYP11B2 Assay as compared to the V79-Human-CYP11B1 Assay.

Due to their ability to inhibit CYP11B2, the compounds of the present invention may be useful to treat and/or ameliorate the risk for hypertension, hypokalemia, renal failure (e.g., chromic renal failure), restenosis, Syndrome X, nephropathy, post-myocardial infarction, coronary heart diseases, increased formation of collagen, fibrosis and remodeling following hypertension and endothelial dysfunction, cardiovascular diseases, renal dysfunction, liver diseases, vascular diseases, cerebrovascular diseases, retinopathy, neuropathy, insulinopathy, endothelial dysfunction, heart failure (e.g., congestive heart failure), diastolic heart failure, left ventricle diastolic dysfunction, diastolic heart failure, systolic dysfunction, ischemia, myocardial and vascular fibrosis, myocardial necrotic lesions, vascular damage, myocardial infarction, left ventricular hypertrophy, cardiac lesions, vascular wall hypertrophy, endothelial thickening or necrosis of coronary arteries.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 30 mg/kg, preferably 0.001 to 20 mg/kg, in particular 0.01 to 10 mg/kg (in each case mg per kg of bodyweight) is appropriate for administration to an adult weighing approximately 75 kg in order to obtain the desired results. The daily dose is preferably administered in a single dose or, in particular when larger amounts are administered, can be divided into several, for example two, three or four individual doses, and may be, for example but not limited to, 0.1 mg, 0.25 mg, 0.5 mg, 0.75 mg, 1 mg, 1.25 mg, 1.5 mg, 2 mg, 2.5 mg, 5 mg, 10 mg, 20 mg, 40 mg, 50 mg, 75 mg, 100 mg, etc., on a daily basis. In some cases, depending on the individual response, it may be necessary to deviate upwards or downwards from the given daily dose.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The tems "preventing" or "prevention" are used herein to refer to administering a compound before the onset of clinical symptoms.

It is understood that a specific daily dosage amount can simultaneously be both a therapeutically effective amount, e.g., for treatment of hypertension, and a prophylactically effective amount, e.g., for prevention of myocardial infarction.

In the methods of treatment of this invention, the compound may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred, particularly solid oral dosage units such as pills, tablets or capsules.

Accordingly, this invention also provides pharmaceutical compositions comprised of a compound of Formula I and a pharmaceutically acceptable carrier. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. Pharmaceutical compositions may also contain other customary additives, for example, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. The carrier is comprised of one or more pharmaceutically acceptable excipients. Furthermore, a therapeutically effective amount of a compound of this invention can be used for the preparation of a medicament useful for inhibiting aldosterone synthase, inhibiting CYP11B2, for normalizing a disturbed aldosterone balance, or for treating or preventing any of the medical conditions described herein, in dosage amounts described herein.

The amount of active compound of Formula I and its pharmaceutically acceptable salts in the pharmaceutical composition may be, for example but not limited to, from 0.1 to 200 mg, preferably from 0.1 to 50 mg, per dose on a free acid/free base weight basis, but depending on the type of the pharmaceutical composition and potency of the active ingredient it could also be lower or higher. Pharmaceutical compositions usually comprise 0.5 to 90 percent by weight of the active compound on a free acid/free base weight basis.

Since the compounds of Formula I inhibit aldosterone synthase, apart from use as pharmaceutically active compounds in human medicine and veterinary medicine, they can also be employed as a scientific tool or as aid for biochemical investigations in which such an effect on aldosterone synthase and aldosterone levels is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents (or therapeutic agents) may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme (ACE) inhibitors (e.g, alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists (e.g., candesartan, eprosartan, irbesartan, losartan, olmesartan, telmisartan, valsartan) neutral endopeptidase inhibitors (e.g., thiorphan and phosphoramidon), aldosterone antagonists, renin inhibitors (e.g., enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, bepridil, diltiazem, felodipine, gallopamil, nicardipine, nifedipine, niludipine, nimodipine, nisoldipine veraparmil), potassium channel activators (e.g., nicorandil, pinacidil, cromakalim, minoxidil, aprilkalim, loprazolam), diuretics (e.g., hydrochlorothiazide); including loop diuretics such as ethacrynic acid, furosemide, bumetanide and torsemide, sympatholitics, beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly in niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, metformin, rosiglitazone), dipeptidyl peptidase 4 inhibitors (e.g., sitagliptin, alogliptin, vildagliptin, saxagliptin, linagliptin, dutogliptin, and gemigliptin); or with other drugs beneficial for the prevention or the treatment of the above-mentioned diseases including nitroprusside and diazoxide.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods and one skilled in the art would have resources such as *Chemical Abstracts* or *Beilstein* at his or her disposal to assist in devising an alternative method of preparing a specific compound.

The compounds of the present invention can be prepared according to the procedures of the following Schemes using appropriate materials and are further exemplified by the specific Examples which follow. Moreover, by utilizing the procedures described herein, one of ordinary skill in the art can readily prepare additional compounds of the present invention claimed herein.

Throughout the synthetic schemes, abbreviations are used with the following meanings unless otherwise indicated: AcCN=acetonitrile; aq=aqueous, Ar=aryl; BSA=bovine serum albumin; Bu=butyl, t-Bu=tert-butyl; n-BuLi=n-butyllithium; CELITE=diatomaceous earth; conc, conc.=concentrated; c-Pr=cyclopropyl; Cy=cyclohexyl; DECALIN=decahydronaphthalene; dba=dibenzylideneacetone; DCM=dichloromethane; dffp=1,1'-bis(diphenylphosphino)ferrocene; DIPA=dissopropyl amine; DMEM=Dulbecco's modified eagle medium; DMF=N,N-dimethylformamide; DMSO=dimethylsulfoxide; eq.=equivalent(s); EDTA=ethylenediaminetetraacetic acid; Et=ethyl; EtOAc=ethyl acetate; EtOH=ethanol; FBS=Fetal Bovine Serum; h, hr=hour; HAS=hydroxylamine-o-sulphonic acid; HPLC=High pressure liquid chromatography; HTRF=homogenous time resolved fluorescence; i-PrOH=isopropanol; i-Pr=isopropyl; LCMS=liquid chromatography-mass spectroscopy; Me=methyl; MeOH=methanol; min, min.=minute; MS=mass spectroscopy; NCS=N-chlorosuccinimide; NMR=nuclear magnetic resonance; PBS=phosphate buffered saline; PdCl$_2$(dppf)=dichloro[1,1'-bis(diphenylphosphino) ferrocene]palladium(II); Pd$_2$(dba)$_3$=tris(dibenzylidineacetone)dipalladium; Pd(dppf)$_2$Cl$_2$=1,1-bis(diphenylphosphino)-ferrocene]dichloropalladium(II); Pd/C=palladium on activated carbon; Ph=phenyl; Pr=propyl; Py=pyridyl; PyBOP=(benzotriazol-1-yloxy)tripyrrolidinophosphonium hexafluorophosphate; OAc=acetate; RT, rt=room temperature; sat.=saturated; S-Phos=2-dichlorocyclohexylphosphino-2',6'-dimethoxybiphenyl; TBAF=tetrabutylammonium fluoride; THF=tetrahydrofuran; triflate, and TfO$_2$=trifluoromethanesulfonic anhydride.

As will be known to those skilled in the art, in all schemes, the products of Formula I and all synthetic intermediates may be purified from unwanted side products, reagents and solvents by recrystallization, trituration, preparative thin layer chromatography, flash chromatography on silica gel as described by W. C. Still et al, J. Org. Chem. 1978, 43, 2923, or reverse-phase HPLC. Compounds purified by HPLC may be isolated as the corresponding salt.

Additionally, in some instances the final compounds of Formula I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chomatography using a homochiral stationary phase and, in the case of cis/trans isomers and diastereomers, normal-phase and reverse-phase chromatography.

Chemical reactions were monitored by LCMS, and the purity and identity of the reaction products were assayed by LCMS (electrospray ionization) and NMR. LCMS spectra were recorded in some instances, for example, on an Agilent 1100 series instrument equipped with an Xterra MS C18 column (3.5 μM, 3.0×50 mm i.d.) and UV detector. 1H NMR spectra were recorded, for example, on a Varian 500 HHz spectrometer and are internally referenced to residual protio solvent signals. Data for $^1$H NMR are reported with chemical shift (δ ppm), multiplicity (s=singlet, d=doublet, t=triplet, q=quartet, m=multiplet, br s=broad singlet, br m=broad multiplet), coupling constant (Hz), and integration. Unless otherwise noted, all LCMS ions listed are [M+H]. All temperatures are degrees Celsius unless otherwise noted.

In the Examples, some intermediates and final compounds having a chiral carbon were prepared as racemates, and some chiral intermediates were resolved and the enantiomers were used separately to synthesize enantiomeric downstream intermediates and final products. In some cases racemic final products may have been resolved. In the instances where chiral compounds were separated by chiral HPLC purification, the term "enantiomer A" or "ent A" refers to the first eluting enantiomer and the downstream compounds derived from this enantiomer. The term "enantiomer B" or "ent B" refers to the second eluting enantiomer and the downstream compounds derived from this enantiomer. The term "rac" refers to a racemic mixture. As a result, the chemical nomenclature may indicate that an S and/or an R enantiomer was obtained, but the absolute stereochemistry of the separate enantiomers A and/or B was not determined.

Preparative HPLC was performed, for example, using a SunFire Prep C18 OBD column (5 μM, 19×100 mm i.d.) on Gilson instruments equipped with UV detectors.

Flash chromatography on silica gel was performed, for example, using pre-packed silica gel columns on Biotage Horizon or Biotage SP-1 instruments equipped with UV detectors.

The following examples are provided so that the invention might be more fully understood. They should neither be construed as forming the only genus that is considered as the invention nor limiting the invention in any way.

Scheme 1

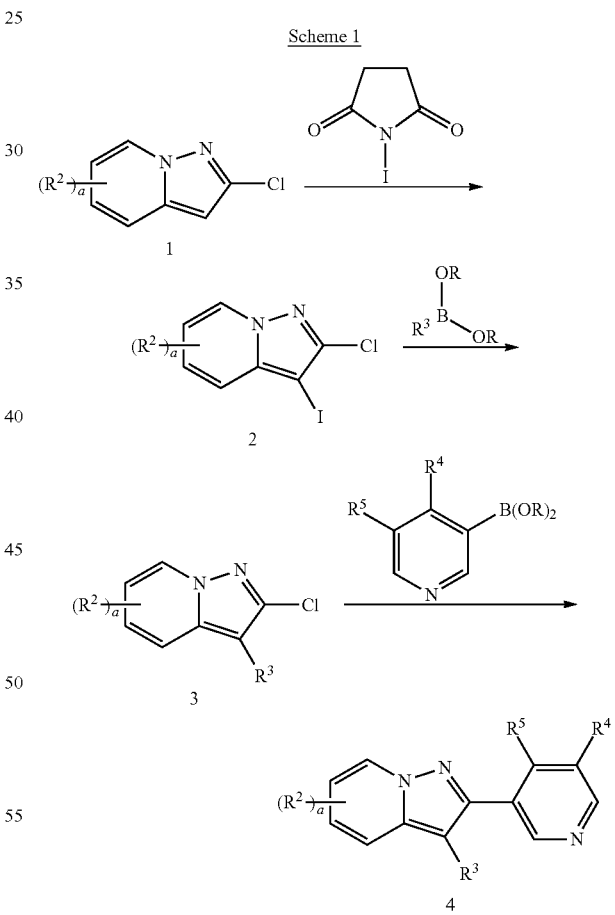

2-Heteroaryl pyrazolopyridines can be synthesized according to Scheme 1. 2-Chloro pyrazolopyridine 1 can be treated with NIS to yield 2-chloro-3-iodo pyrazolopyridine 2 which can be converted to 3-substituted 2-chloro pyrazolopyridine 3 under Suzuki conditions. Further Suzuki reaction of 3 with an appropriate heteroaryl boronate affords the desired 2-heteroaryl pyrazolopyridine 4.

Scheme 2

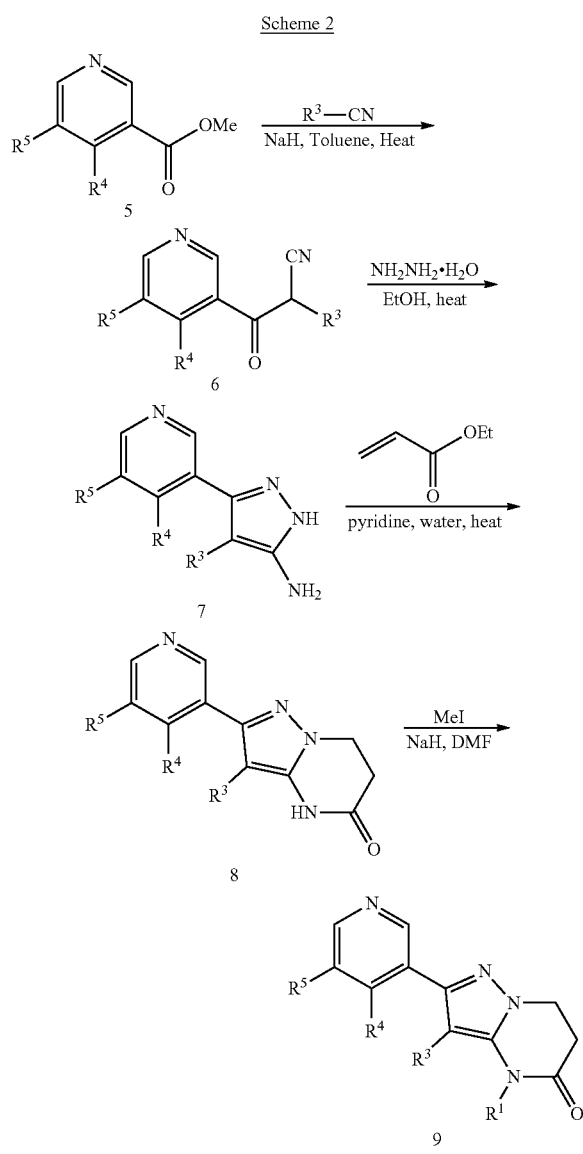

5-Oxo-2-heteroaryl-tetrahydropyrazolo pyrimidines can be synthesized according to Scheme 2. Reaction of pyridyl ester 5 with an appropriate nitrile yields 2-substituted 3-oxo-3-heteroaryl propanenitrile 6 which upon treatment with hydrazine hydrate may be converted to heteroaryl aminopyrazole 7. Reaction of 7 with ethyl acrylate affords 5-oxo-2-heteroaryl-tetrahydropyrazolo pyrimidine 8 which can be alkylated with methyl iodide to afford 4-methyl-5-oxo-2-heteroaryl-tetrahydropyrazolo pyrimidine 9.

Scheme 3

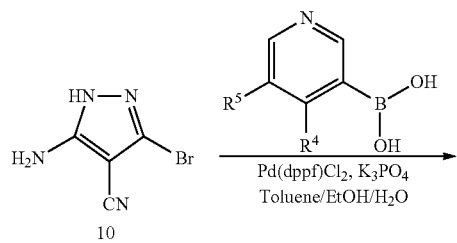

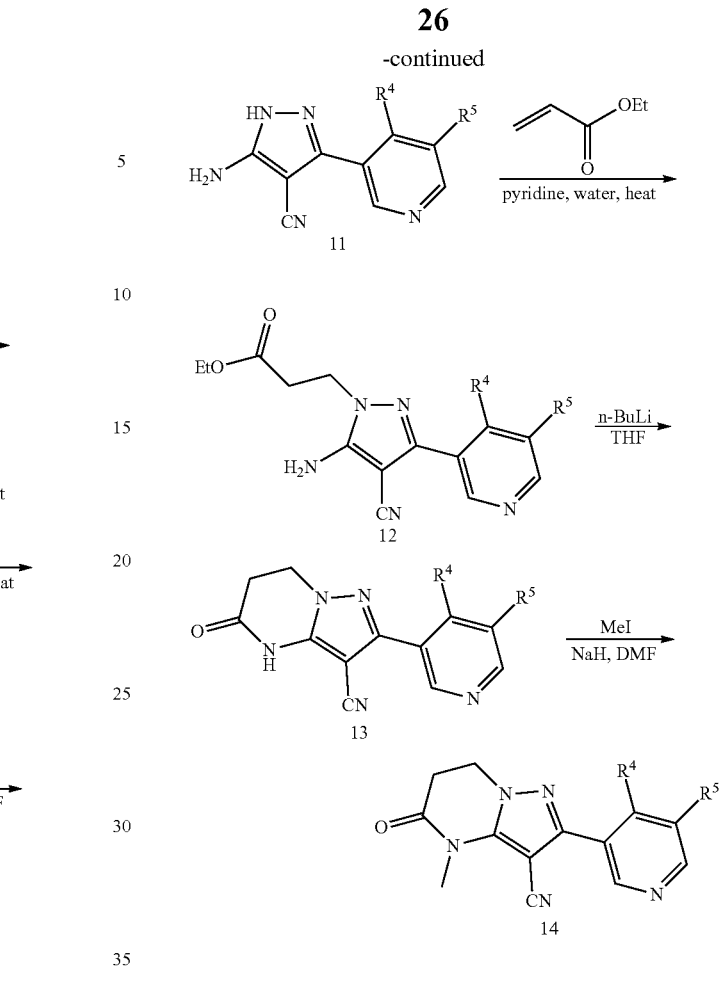

5-Oxo-2-heteroaryl-tetrahydropyrazolo-pyrimidine-3-carbonitriles can be prepared according to Scheme 3. Suzuki coupling between 5-amino-3-bromo-1H-pyrazole-4-carbonitrile 10 and a pyridyl boronic acid affords 3-cyano-heteroaryl-aminopyrazole 11. Treatment of 11 with ethyl acrylate yields alkylated 3-cyano-heteroaryl-aminopyrazole 12. Ring closure of 12 upon reaction with n-butyl lithium yields 5-oxo-2-heteroaryl-tetrahydropyrazolo-pyrimidine-3-carbonitriles 13 which can be further alkylated with methyl iodide to afford 4-methyl-5-oxo-2-heteroaryl-tetrahydropyrazolo pyrimidine 14.

The heteroaryl boronic acids or esters employed in these reactions may be obtained commercially, prepared by reactions known in literature or prepared by modifying reactions known in the art. Scheme 4 depicts one method, for example, by which one of ordinary skill in the art may be able to prepare a boronic ester:

Scheme 4

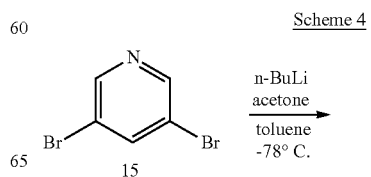

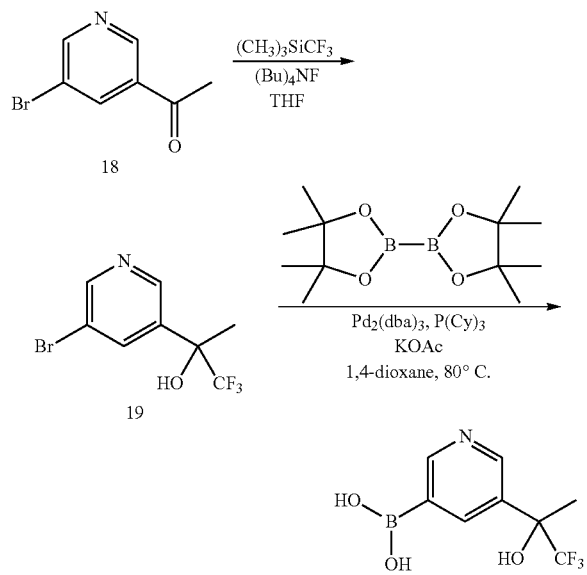

Treating 3,5-dibromopyridine 15 with n-butyllithium and acetone in a solvent such as toluene at low temperature provides 16. Heating bromide 16 and 4,4,4',4',5,5,5',5'-octamethyl-2,2'-bi-1,3,2-dioxaborolane in the presence of a catalyst such as dichloro[1,1'-bis(diphenylphosphino)ferrocene]palladium (II) and a base such as potassium acetate in a solvent such as 1,4-dioxane then affords boronate ester 17.

Scheme 5 describes an alternative method for the preparation of pyridyl boronic acids:

Scheme 5

1-(5-Bromopyridin-3-yl)ethanone 18 is treated with (trifluoromethyl)trimethylsilane and tetrabutylammonium fluoride in a solvent such as tetrahydrofuran to provide 19. Heating of bromide 19 and 4,4,4',4',5,5,5',5'-octamethyl-2,2'-bi-1,3,2-dioxaborolane in the presence of a catalyst such as tris (dibenzylideneacetone)dipalladium (0), a ligand such as tricyclohexylphosphine, and a base such as potassium acetate in a solvent such as 1,4-dioxane then affords boronic acid 20.

As will be known to those skilled in the art, in all schemes, the products of Formula I and all synthetic intermediates may be purified from unwanted side products, reagents and solvents by recrystallisation, trituration, preparative TLC, flash chromatography on silica gel or reverse-phase HPLC. Compounds purified by HPLC may be isolated as the corresponding salt.

The following is illustrative of the process used for making some of the intermediates employed in the examples below:

Intermediate B

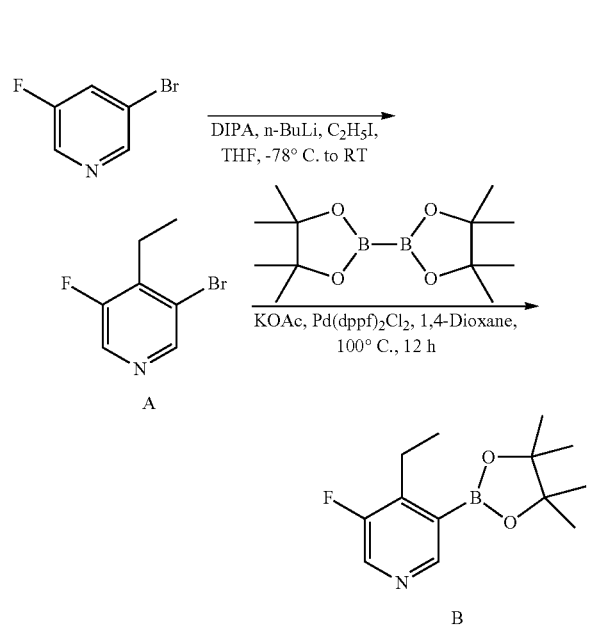

Synthesis of 3-bromo-5-fluoro-4-ethyl pyridine (A)

n-butyl lithium (92.3 mL, 0.147 mol, 1.6 M) was added to a solution of diisopropyl amine (20.1 mL, 0.147 mol) in tetrahydrofuran (120 mL) at −78° C. and allowed to stir for 30 min at 0° C. The reaction mixture was cooled to −78° C. and a solution of 3-bromo-5-fluoro-pyridine (20.0 g, 0.113 mol) in tetrahydrofuran (20 mL) was added and stirred for 30 min. Ethyl iodide (8.85 mL, 0.124 mol) was added to reaction mixture and allowed to stir at room temperature for 2 h. The reaction mixture was quenched with saturated ammonium chloride (100 mL) solution and extracted with ethyl acetate (3×200 mL). The combined organic extracts were washed with saturated sodium chloride, dried over sodium sulphate and concentrated to provide 3-bromo-5-fluoro-4-ethyl pyridine. $^1$H NMR (400 MHz, CDCl$_3$) δ 8.49 (s, 1 H), 8.31 (s, 1 H), 2.87-2.82 (m, 2 H), 1.22-1.19 (t, J=4.0 Hz, 3 H). MS (M+1): 205.8.

Synthesis of 4-ethyl-3-fluoro-5-(4,4,5,5-tetramethyl-1,3,2-dioxaborolan-2-yl)pyridine (B)

A reaction vessel containing a mixture of 3-bromo-4-ethyl-5-fluoropyridine (0.25 g, 0.0012 mol), 4,4,4',4',5,5,5',5'-octamethyl-2,2'-bi(1,3,2-dioxaborolane) (0.96 g, 0.0036 mol), and potassium acetate (0.36 g, 0.0036 mol) in 1,4-dioxane (15 mL) was purged with argon for 10 min. Next [1,1-bis(diphenylphosphino)-ferrocene]dichloropalladium(II) (0.09 g, 0.00012 mol) was added and heated at 100° C. for 18 h. The reaction mixture was cooled to room temperature filtered through a bed of CELITE and the bed was washed with ethyl acetate. The filtrate was concentrated under reduced pressure to afford the crude product 4-ethyl-3-fluoro-5-(4,4,5,5-tetramethyl-1,3,2-dioxaborolan-2-yl)pyridine. MS (M+1): 252.1.

Intermediate C

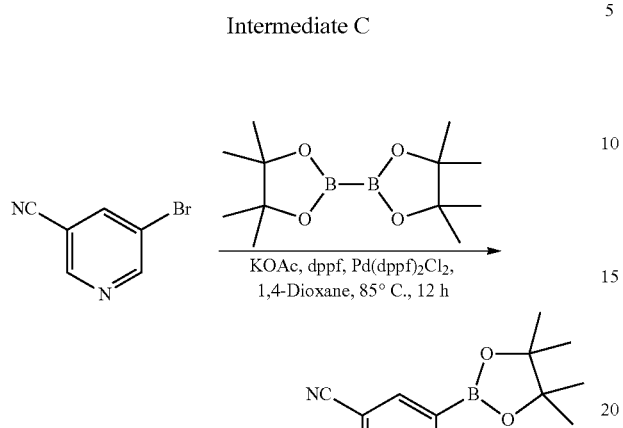

Synthesis of 5-(4,4,5,5-tetramethyl-1,3,2-dioxaborolan-2-yl)nicotinonitrile (C)

A reaction vessel containing a mixture of 5-bromonicotinonitrile (0.5 g, 2.73 mmol), 4,4,4',4',5,5,5',5'-octamethyl-2,2'-bi(1,3,2-dioxaborolane) (0.93 g, 3.54 mmol), and potassium acetate (0.80 g, 8.19 mmol) in 1,4-dioxane (30 mL) was purged with argon for 10 min. Next, 1,1'-bis(diphenylphosphino)ferrocene (0.045 g, 0.0819 mmol) and [1,1-bis(diphenylphosphino)-ferrocene]dichloropalladium(II) (0.066 g, 0.0819 mmol) were added and the reaction mixture was heated at 85° C. for 12 h. The reaction mixture was cooled to room temperature filtered through a bed of CELITE and the bed was washed with ethyl acetate. The filtrate was concentrated under reduced pressure to afford the crude product 5-(4,4,5,5-tetramethyl-1,3,2-dioxaborolan-2-yl)nicotinonitrile. MS (M+1): 231.1.

Intermediate D

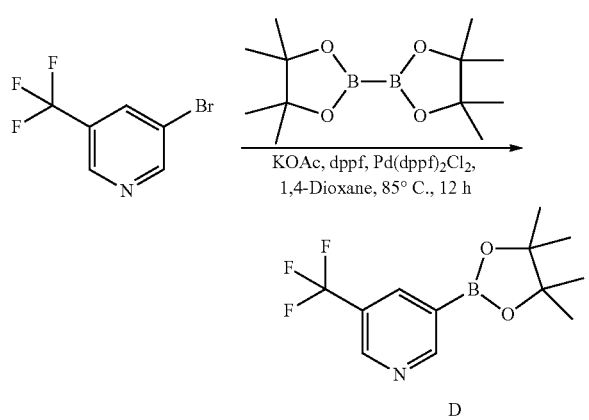

Synthesis of 3-(4,4,5,5-tetramethyl-1,3,2-dioxaborolan-2-yl)-(trifluoromethyl)-pyridine (D)

A reaction vessel containing a mixture of 5-bromonicotinonitrile (0.5 g, 2.212 mmol), 4,4,4',4',5,5,5',5'-octamethyl-2,2'-bi(1,3,2-dioxaborolane) (0.75 g, 2.87 mmol), and potassium acetate (0.65 g, 6.636 mmol) in 1,4-dioxane (30 mL) was purged with argon for 10 min. Next, 1,1'-bis(diphenylphosphino)ferrocene (0.036 g, 0.066 mmol) and [1,1-bis(diphenylphosphino)-ferrocene]dichloropalladium(II) (0.04 g, 0.049 mmol) were added and the reaction mixture was heated at 85° C. for 12 h. The reaction mixture was cooled to room temperature filtered through a bed of CELITE and the bed was washed with ethyl acetate. The filtrate was concentrated under reduced pressure to afford the crude product 3-(4,4,5,5-tetramethyl-1,3,2-dioxaborolan-2-yl)-5-(trifluoromethyl)pyridine. MS (M+1): 274.1.

Intermediate E

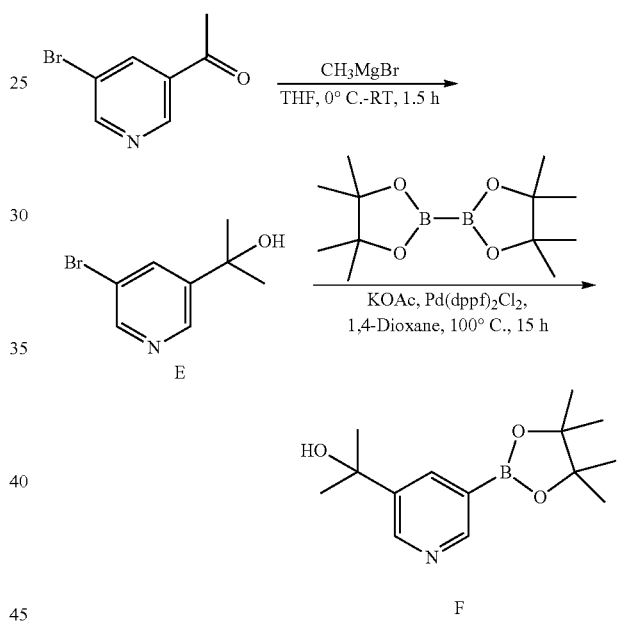

Synthesis of 2-(5-bromopyridin-3-yl)propan-2-ol (E)

Methyl magnesium bromide (5.3 mL, 0.075 mol) was added to a stirred solution of 1-(5-bromopyridin-3-yl)ethanone (1.0 g, 0.05 mol) in tetrahydrofuran (20.0 mL), cooled to 0° C. and the resulting mixture was allowed to warm to room temperature and stirred for 1.5 h. The reaction mixture was quenched with 1N hydrochloric acid (20 mL) and extracted with ethyl acetate (2×75 mL). The combined organic layers were dried over sodium sulphate and concentrated under vacuum to afford the crude compound which was purified by column chromatography to obtain 2-(5-bromopyridin-3-yl)propan-2-ol. MS (M+1): 217.1.

Synthesis of 2-(5-(4,4,5,5-tetramethyl-1,3,2-dioxaborolan-2-yl)pyridin-3-yl)propan-2-ol (F)

A reaction vessel containing a mixture of 2-(5-bromopyridin-3-yl)propan-2-ol (0.5 g, 2.31 mmol), 4,4,4',4',5,5,5',5'-octamethyl-2,2'-bi(1,3,2-dioxaborolane) (2.4 g, 9.2 mmol), and potassium acetate (0.612 g, 6.9 mmol) in 1,4-dioxane (20 mL) was purged with argon for 10 min. Next, [1,1-bis(diphenylphosphino)-ferrocene]dichloropalladium (II) (0.190 g, 0.23 mmol) was added and the reaction mixture was heated at 100° C. for 15 h. The reaction mixture was cooled to room temperature then filtered through a bed of CELITE and the bed was washed with ethyl acetate. The filtrate was concentrated under reduced pressure to afford the crude product 2-(5-(4,4,5,5-tetramethyl-1,3,2-dioxaborolan-2-yl)pyridin-3-yl)propan-2-ol. MS (M+1): 265.1.

Intermediate I

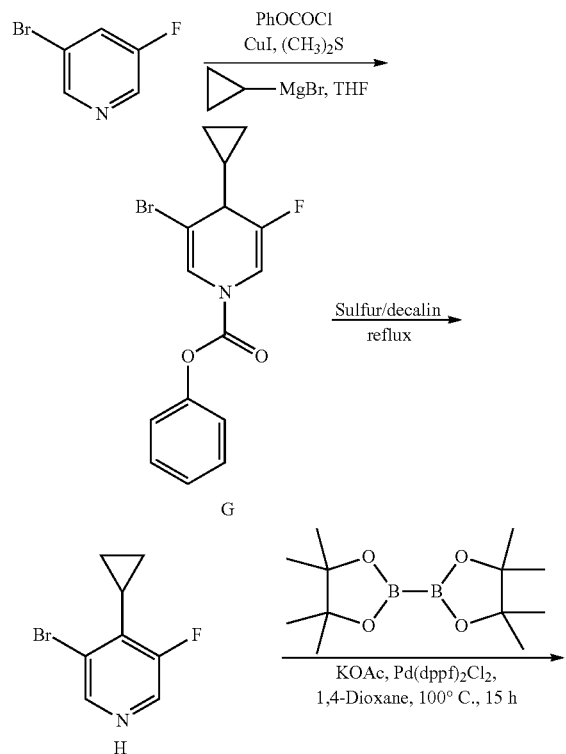

Synthesis of phenyl 3-bromo-4-cyclopropyl-5-fluoropyridine-1(4H)-carboxylate (G)

Phenyl chloroformate (0.764 mL, 0.0060 mol) was added to a mixture of copper iodide (1.082 g, 0.0056 mol), dimethylsulphide (2.78 mL, 0.0380 mol) and 3-bromo-5-fluoropyridine (1.0 g, 0.0056 mol) in anhydrous tetrahydofuran (25 mL) at room temperature and the mixture was stirred for 40-50 min. To this suspension cyclopropyl magnesium bromide (12.13 mL, 0.0060 mol, 0.5M solution in tetrahydofuran) was added at −25 to −20° C. over 30-40 min. The mixture was stirred at this temperature for 30 min, and then warmed slowly to room temperature over 1.0-1.5 h. The reaction mixture was quenched with 20% ammonium chloride (25 mL), followed by extraction of the aqueous layer with ethyl acetate (50 mL). The organic layer was washed with 20% ammonium chloride (25 mL), then saturated sodium chloride (25 mL), and dried over anhydrous sodium sulphate. Silica gel chromatography using 0-5% ethyl acetate-hexane gradient yielded crude phenyl 3-bromo-4-cyclopropyl-5-fluoropyridine-1 (4H)-carboxylate MS (M+1): 339.7.

Synthesis of 3-bromo-4-cyclopropyl-5-fluoropyridine (H)

A mixture of the crude phenyl 3-bromo-4-cyclopropyl-5-fluoropyridine-1 (4H)-carboxylate (1.14 g, 0.0034 mol) and sulphur (0.108 g, 0.0034 mol) were heated at reflux in DECALIN (10 mL) for a period of 3 h, then cooled to room temperature. Purification by silica gel chromatography, eluting first with hexanes, then with a 2-5% ethyl acetate-hexane gradient, gave the title compound. MS (M+1): 217.1.

Synthesis of 4-cyclopropyl-3-fluoro-5-(4,4,5,5-tetramethyl-1,3,2-dioxaborolan-2-yl)pyridine (I)

A reaction vessel containing a mixture of 3-bromo-4-cyclopropyl-5-fluoropyridine (0.3 g, 0.0013 mol), 4,4,4',4',5,5,5',5'-octamethyl-2,2'-bi(1,3,2-dioxaborolane) (1.4 g, 0.005 mol), and potassium acetate (0.367 g, 0.0039 mol) in 1,4-dioxane (10 mL) was purged with argon for 10 min. Next [1,1-bis(diphenylphosphino)-ferrocene]dichloropalladium (II) (0.113 g, 0.00013 mol) was added and the reaction mixture was heated at 100° C. for 15 h. The reaction mixture was cooled to room temperature filtered through a bend of CELITE and the bed was washed with ethyl acetate. The filtrate was concentrated under reduced pressure to afford the crude product 4-cyclopropyl-3-fluoro-5-(4,4,5,5-tetramethyl-1,3,2-dioxaborolan-2-yl)pyridine MS (M+1): 264.1.

Intermediate K

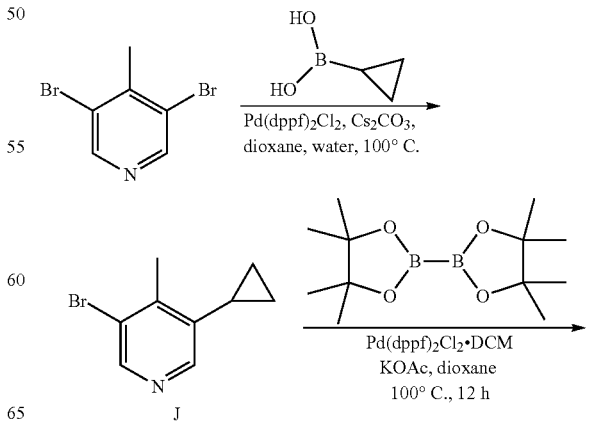

33
-continued

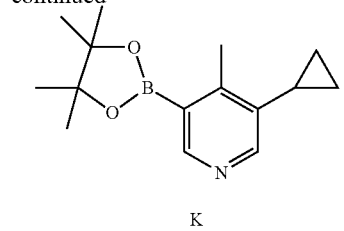

K

Synthesis of 3-bromo-5-cyclopropyl-4-methylpyridine (J)

Cesium carbonate (2.59 g, 0.00797 mol) was added to a stirred solution of 3,5-dibromo-4-methylpyridine (1.0 g, 0.0039 mol) and cyclopropylboronic acid (0.34 g, 0.0039 mol) in the mixture of 1,4-dioxan (35 mL) and water (15 mL). The reaction mixture was purged with argon for 20 min. Next, $Pd(dppf)_2Cl_2$ (0.14 g, 0.000199 mol) was added. The reaction mixture was heated at 100° C. and for 6 h. It was cooled to room temperature, filtered through a bed of CELITE and the bed was thoroughly washed with ethyl acetate. The filtrate was concentrated under vacuum. The residue was dissolved with dichloromethane, washed with water and saturated sodium chloride solution, dried over sodium sulphate, concentrated under vacuum and purified by silica gel (60-120) column chromatography with 0-2.5% ethyl acetate in hexane to afford the title compound. $^1$H NMR (400 MHz, $CdCl_3$) δ 8.51 (s, 1 H), 8.17 (s, 1 H), 2.52 (s, 3 H), 1.87-1.82 (m, 1 H), 1.03-0.99 (m, 2 H), 0.71-0.68 (m, 2 H). MS (M+1): 211.8.

Synthesis of 3-cyclopropyl-4-methyl-5-(4,4,5,5-tetramethyl-1,3,2-dioxaborolan-2-yl)-pyridine (K)

4,4,4',4',5,5,5',5'-octamethyl-2,2'-bi(1,3,2-dioxaborolane) (2.99 g, 0.0117 mol) and potassium acetate (0.46 g, 0.00471 mol) was added to a stirred solution of 3-bromo-5-cyclopropyl-4-methylpyridine (0.5 g, 0.00235 mol) in dioxin (10 mL). The reaction mixture was purged with argon for 20 min. After purging, $Pd(dppf)_2Cl_2$.DCM (0.09 g, 0.000117 mol) was added. The reaction mixture was heated at 100° C. for 12 h. The reaction mixture was cooled to room temperature, filtered the reaction mixture through a bed of CELITE and the bed was thoroughly washed with ethyl acetate. The filtrate was concentrated under vacuum. The residue was dissolved in ethyl acetate and the organic layer was washed with water and saturated sodium chloride solution, dried over sodium sulphate, and concentrated under vacuum to obtain 3-cyclopropyl-4-methyl-5-(4,4,5,5-tetramethyl-1,3,2-dioxaborolan-2-yl)pyridine, which was not further purified. MS (M+1): 178.1 (as boronic acid in LCMS).

EXAMPLE 1

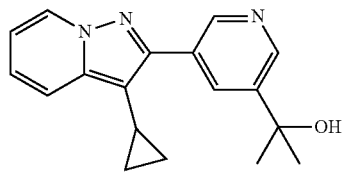 [SMILES: CC(C)(O)c1cncc(-c2nn3ccccc3c2C2CC2)c1]

34

Step A. 2-chloro-3-iodopyrazolo[1,5-a]pyridine

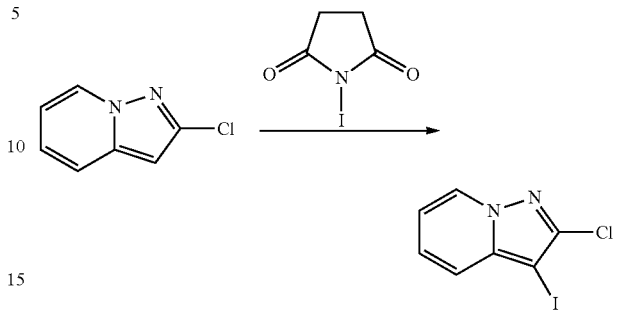

To a solution of 2-chloro-pyrazolo[1,5-a]pyridine (0.500 g, 3.28 mmol) in acetonitrile (16.4 mL) was added N-iodosuccinimide (0.885 g, 3.93 mmol). The resulting mixture was stirred at room temperature for 2 hours, then concentrated under reduced pressure. The resulting residue was diluted with dichloromethane, washed with saturated aqueous sodium chloride solution, dried over $MgSO_4$, filtered and concentrated under reduced pressure. Purification by flash chromatography on silica gel (0-15% ethyl acetate in hexanes) provided the title compound. LCMS m/z 278.72 [M+H]$^+$, 280.64 [M+2+H]$^+$, $^1$H NMR (500 MHz, $CDCl_3$) δ 8.35 (d, J=6.8 Hz, 1 H), 7.38 (d, J=9.0 Hz, 1H), 7.24 (d, J=8.6 Hz, 1 H), 6.84-6.81 (m, 1 H).

Step B. 2-chloro-3-cyclopropylpyrazolo[1,5-a]pyridine

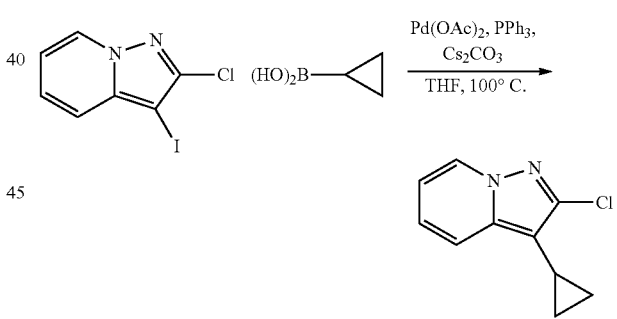

A mixture of the title compound from Example 1 Step A (0.250 g, 0.898 mmol), palladium acetate (0.020 g, 0.090 mmol), cyclopropyl boronic acid (0.154 g, 1.80 mmol), cesium carbonate (0.878 g, 2.69 mol), and triphenylphosphine (0.047 g, 0.180 mmol) in tetrahydrofuran (8.98 mL) was heated in a sealed tube at 100° C. for 18 hours. The reaction mixture was then cooled to room temperature, filtered and concentrated under reduced pressure. Purification of the resulting residue by flash chromatography on silica gel (0-15% ethyl acetate in hexanes) provided the title compound: LCMS m/z 192.93 [M+H]$^+$, 194.89 [M+2+H]$^+$; $^1$H NMR (500 MHz, $CDCl_3$) δ 8.29 (d, J=7.0 Hz, 1 H), 7.49 (d, J=12.8 Hz, 1 H), 7.21 (dd, J=7.5, 7.5 Hz, 1 H), 6.70 (dd, J=6.3, 6.3 Hz, 1 H), 1.79-1.74 (m, 1 H), 0.98-0.95 (m, 2 H), 0.75-0.73 (m, 2 H).

Step C. 2-(5-Bromopyridin-3-yl)propan-2-ol

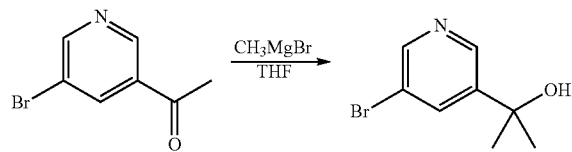

To a cooled (−78° C.) solution of 3-acetyl-5-bromo pyridine (1.98 g, 9.90 mmol) in tetrahydrofuran (33 mL) was added dropwise a solution of methyl magnesium bromide in diethyl ether (3.0 M, 6.60 mL, 19.8 mmol). The reaction was warmed to room temperature, and the resulting mixture was stirred at room temperature overnight. The reaction was then quenched with saturated aqueous ammonium chloride solution and extracted with diethyl ether. The organic extracts were combined, washed with brine, dried over magnesium sulfate, filtered and concentrated. Purification by flash chromatography on silica gel (0-60% ethyl acetate in hexanes) provided the title compound: LCMS m/z 217.83 [M+H]$^+$; $^1$H NMR (500 MHz, CDCl$_3$) δ 8.61 (s, 1 H), 8.53 (s, 1 H), 8.01 (d, J=1.9 Hz, 1 H), 2.38 (br s, 1 H), 1.61 (6 H).

Step D. 2-[5-(4,4,5,5-tetramethyl-1,3,2-dioxaborolan-2-yl)-3-pyridinyl]-2-propanol

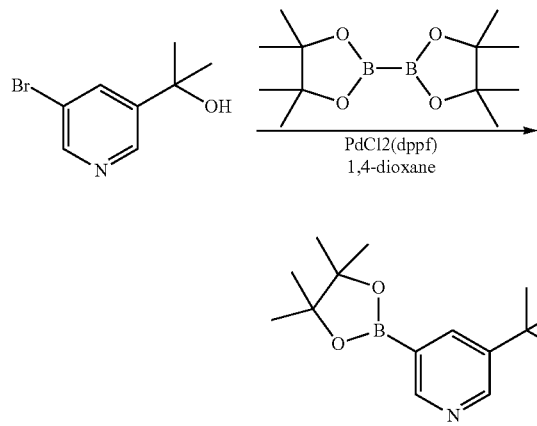

To a 5000-mL 4-necked round-bottom flask purged and maintained with an inert atmosphere of nitrogen were added a solution of the title compound from Example 1 Step C (160 g, 395 mmol) in 1,4-dioxane (2000 mL), 4,4,5,5-tetramethyl-2-(4,4,5,5-tetramethyl-1,3,2-dioxaborolan-2-yl)-1,3,2-dioxaborolane (240 g, 498 mmol), potassium acetate (240 g, 1.63 mol), and PdCl$_2$(dppf) (30 g, 23 mmol). The resulting solution was stirred for 4 hours at 80° C. The reaction was then cooled to room temperature, filtered and concentrated under reduced pressure. The residual solution was diluted with hexanes and filtered. HCl gas was bubbled through the filtrate. The resulting mixture was filtered, and the solids diluted with dichloromethane, then concentrated under reduced pressure. The residue was diluted with H$_2$O, and washed sequentially with diethyl ether, dichloromethane, and hexanes. The aqueous layer was adjusted to pH 7-8 with saturated aqueous sodium carbonate solution, then extracted with dichloromethane. The organic extracts were combined, dried and concentrated under vacuum to afford the title compound: $^1$H NMR (400 MHz, CDCl$_3$): δ 8.83 (s, 1 H), 8.19 (s, 1 H), 1.62 (s, 6 H), 1.36 (s, 12 H).

Step E. 2-(5-(3-cyclopropylpyrazolo[1,5-a]pyridin-2-yl)pyridin-3-yl)propan-2-ol

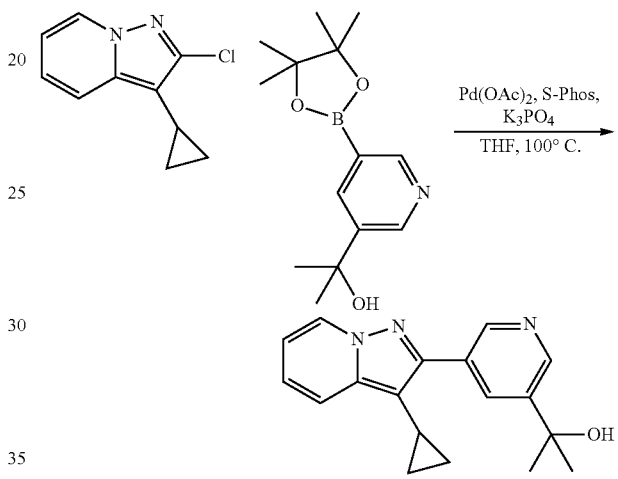

To a solution of the title compound from Example 1 Step D (0.114 g, 0.434 mmol) and the title compound from Example 1 Step B (0.084 g, 0.434 mmol) in tetrahydrofuran (4.34 mL) were added palladium acetate (0.010 g, 0.043 mmol), 2-dicyclohexylphosphino-2',6'-dimethoxy-1,1'-biphenyl (0.036 g, 0.087 mmol), and potassium phosphate tribasic (0.277 g, 1.30 mmol). The resulting mixture was heated at 100° C. for 18 hours, then filtered and concentrated under reduced pressure. Purification by column chromatography on silica gel (0-25% ethyl acetate in hexanes) provided the title compound: LCMS m/z 293.86 [M+H]$^+$; $^1$H NMR (500 MHz, CDCl$_3$) δ 9.16 (s, 1H), 8.76 (s, 1 H), 8.45 (dd, J=2.0, 2.0 Hz, 1 H), 7.66 (d, J=8.8 Hz, 1 H), 7.11 (d, J=6.9 Hz, 1 H), 6.75 (dd, J=6.7, 6.7 Hz, 1 H), 2.45 (br s, 1 H), 2.01-1.98 (m, 1 H), 1.68 (s, 6 H), 1.01 (d, J=8.0 Hz, 2 H), 0.50 (d, J=5.0 Hz, 2 H).

EXAMPLE 2

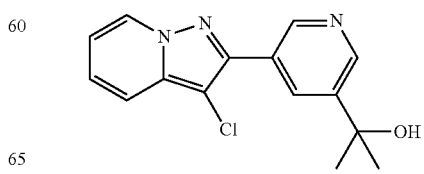

Step A. 2-(5-(pyrazolo[1,5-a]pyridin-2-yl)pyridin-3-yl)propan-2-ol

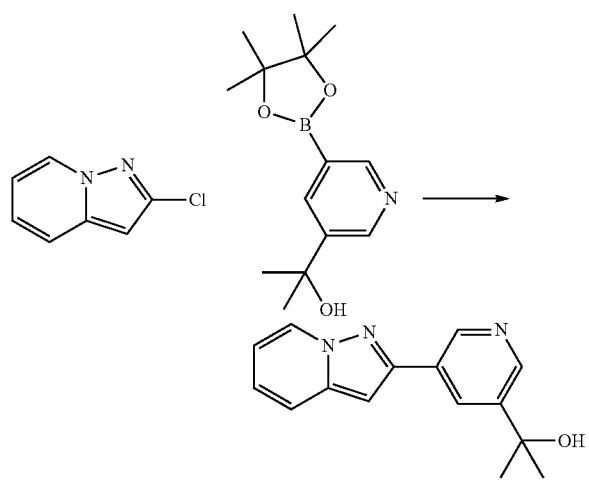

To a solution of 2-chloro-pyrazolo[1,5-a]pyridine (0.200 g, 1.31 mmol) and the title compound from Example 1 Step D (0.414 g, 1.573 mmol) in tetrahydrofuran (6.55 mL) were added palladium acetate (0.029 g, 0.131 mmol), 2-dicyclohexylphosphino-2',6'-dimethoxy-1,1'-biphenyl (0.108 g, 0.262 mmol), and potassium phosphate tribasic (0.835 g, 3.93 mmol). The resulting mixture was heated at 100° C. for 18 hours, then diluted with ethyl acetate, filtered, and concentrated under reduced pressure. Purification by flash chromatography on silica gel (0-15% ethyl acetate in hexanes) provided the title compound: LCMS m/z 254.02 [M+H]$^+$; $^1$H NMR (500 MHz, CDCl$_3$) δ 9.05 (s, 1 H), 8.74 (s, 1 H), 8.49 (d, J=6.9 Hz, 2 H), 8.40 (s, 1 H), 7.55 (d, J=6.9 Hz, 2 H), 7.15 (dd, J=7.6, 7.9 Hz, 1 H), 6.86 (s, 1 H), 6.79 (dd, J=7.1, 6.6 Hz, 1 H), 1.68 (s, 6 H).

Step B. 2-(5-(3-chloropyrazolo[1,5-a]pyridin-2-yl)pyridin-3-yl)propan-2-ol

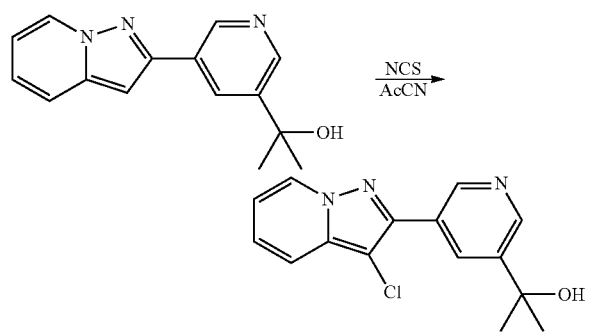

A solution of the title compound from Example 2 Step A (0.099 g, 0.391 mmol) and N-chlorosuccinimide (0.063 g, 0.469 mmol) in acetonitrile (1.95 ml) was stirred at room temperature for 2 hours. The reaction was then concentrated under reduced pressure, diluted with dichloromethane, washed with saturated aqueous sodium chloride solution, dried over MgSO$_4$, filtered and concentrated under reduced pressure.

Purification by column chromatography (70-90% ethyl acetate in hexanes) provided the title compound: LCMS m/z 287.94 [M+H]$^+$, 289.87 [M+2+H]$^+$; $^1$H NMR (500 MHz, CDCl$_3$) δ 9.21 (d, J=1.7 Hz, 1 H), 8.81 (d, J=2.1 Hz, 1 H), 8.48-8.44 (m, 2H), 7.58 (d, J=9.0 Hz, 1 H), 7.24 (dd, J=7.8, 0.9 Hz, 1 H), 6.88-6.85 (m, 1 H), 2.06 (br s, 1 H), 1.69 (s, 6 H).

Intermediate 1

Step A. 2-chloro-3-methylpyrazolo[1,5-a]pyridine

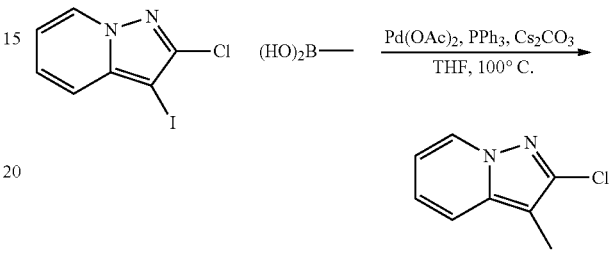

A mixture of the title compound from Example 1 Step A (0.30 g, 1.077 mmol), palladium acetate (0.024 g, 0.108 mmol), methyl boronic acid (0.129 g, 2.155 mmol), cesium carbonate (1.053 g, 3.23 mol) and triphenylphosphine (0.057 g, 0.215 mmol) in tetrahydrofuran (5.39 mL) was heated in a sealed tube at 100° C. for 18 hours. The reaction was then cooled to room temperature, filtered and concentrated under reduced pressure. Purification by column chromatography on silica gel (0-15% ethyl acetate in hexanes) provided the title compound: LCMS m/z 166.94 [M+H]$^+$, 168.89 [M+2+H]$^+$; $^1$H NMR (500 MHz, CDCl$_3$) δ 8.30 (d, J=6.9 Hz, 1 H), 7.35 (d, J=8.9 Hz, 1 H), 7.10 (dd, J=7.7, 7.7 Hz, 1 H), 6.70 (dd, J=6.6, 6.6 Hz, 1 H), 2.30 (d, J=1.2 Hz, 3 H).

Intermediate 2

Step A. 2-chloropyrazolo[1,5-a]pyridine-3-carbonitrile

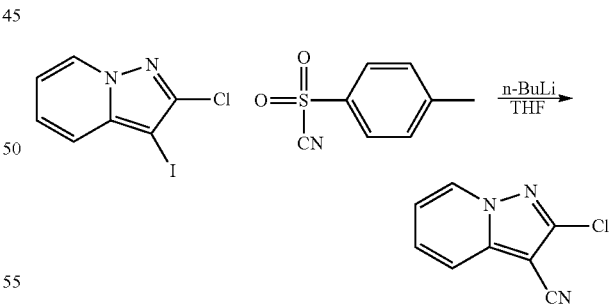

To a cooled –78° C. solution of the title compound from Example 1 Step A (0.20 g, 0.718 mmol) in tetrahydrofuran (3.59 ml) was added a solution of n-butyllithium in hexane (1.6 M, 0.494 ml, 0.790 mmol). After 5 minutes, p-toluenesulfonyl cyanide (0.169 g, 0.934 mmol) was added, and the resulting reaction mixture was allowed to warm to room temperature. After 18 hours, the mixture was concentrated under reduced pressure. Purification by column chromatography on silica gel (0-30% ethyl acetate in hexanes) provided the title compound: LCMS m/z 177.91 [M+H]$^+$, 179.86

[M+2+H]+; 1H NMR (500 MHz, CDCl3) δ 8.47 (d, J=6.9 Hz, 1 H), 7.70 (d, J=9.0 Hz, 1 H), 7.52 (dd, J=8.0, 8.0 Hz, 1 H), 7.26-7.20 (m, 1 H).

Examples listed below in Table 1 were prepared according to the procedures given above for the preparation of Examples 1 and 2 and Intermediates 1 and 2 using the appropriate commercially available starting materials.

TABLE 1

| Example | Structure | Name | LCMS |
|---|---|---|---|
| 3 | 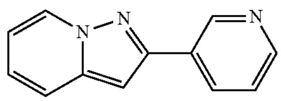 [SMILES: c1cncc(-c2cc3ccccn3n2)c1] | 2-(pyridin-3-yl) pyrazolo[1,5-a]pyridine | 196.06 |
| 4 | 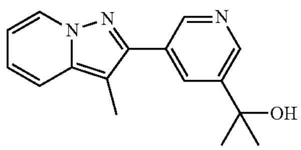 [SMILES: Cc1c(-c2cncc(C(C)(C)O)c2)nn2ccccc12] | 2-(5-(3-methylpyrazolo[1,5-a]pyridin-2-yl) pyridin-3-yl)propan-2-ol | 268.08 |
| 5 | 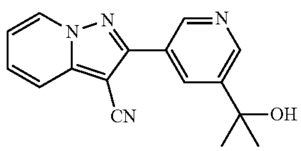 [SMILES: CC(C)(O)c1cncc(-c2nn3ccccc3c2C#N)c1] | 2-(5-(2-hydroxypropan-2-yl)pyridin-3-yl) pyrazolo[1,5-a]pyridine-3-carbonitrile | 279.01 |

EXAMPLE 6

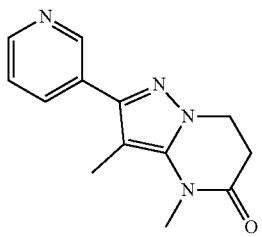 [SMILES: Cc1c(-c2cccnc2)nn2c1N(C)C(=O)CC2]

Step A.
2-methyl-3-oxo-3-(pyridin-3-yl)propanenitrile

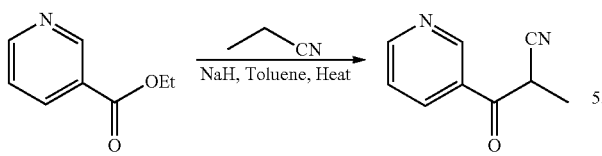

Under a N2 atmosphere ethyl nicotinate (3 g, 0.02 mol) and NaH (1.6 g, 0.04 mol) were suspended in toluene (30 mL) and heated to 90° C. Propiononitrile (2.2 g, 0.04 mol) was added dropwise and the reaction was stirred at 90° C. overnight. After cooling to room temperature, the solid was filtered and collected. The solid was dissolved in water (50 mL) and washed with ethyl acetate (30 mL). The aqueous layer was adjusted to pH=6 with 2M HCl and extracted again with ethyl acetate (30 mL×2). The combined ethyl acetate extracts were combined and dried over Na2SO4, filtered and concentrated in vacuo to give the desired product: 1HNMR (400 MHz, CDCl3) δ 9.25 (d, 1 H, J=1.2 Hz), 8.90 (d, 1 H, J=4.8 Hz), 8.33 (d, 1 H, J=8.0 Hz), 7.54 (dd, 1 H, J=1.2 Hz, J=8.0 Hz), 4.37-4.39 (m, 1 H), 1.71 (d, 3 H, J=7.2 Hz).

Step B. 4-methyl-3-(pyridin-3-yl)-1H-pyrazol-5-amine

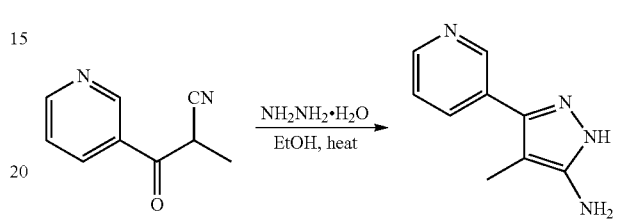

To a solution of 2-methyl-3-oxo-3-(pyridin-3-yl) propanenitrile (1.5 g, 9.4 mmol) in EtOH (20 mL) was added 85% hydrazine hydrate (2 mL). The resulting mixture was heated to reflux for 2 hours. After cooling to rt, the solvent was removed in vacuo and the crude product purified by column chromatography (DCM:MeOH=10:1) to give the desired product: MS (m/z): 175.0 [M+H]+, 1HNMR (400 MHz, CD3OD) δ 8.71 (d, 1H, J=2.0 Hz), 8.50-8.51 (m, 1H), 7.99 (d, 1H, J=8.0 Hz), 7.50-7.55 (m, 1H), 2.06 (s, 3H).

Step C. 3-methyl-2-(pyridin-3-yl)-6,7-dihydropyrazolo[1,5-a]pyrimidin-5(4H)-one

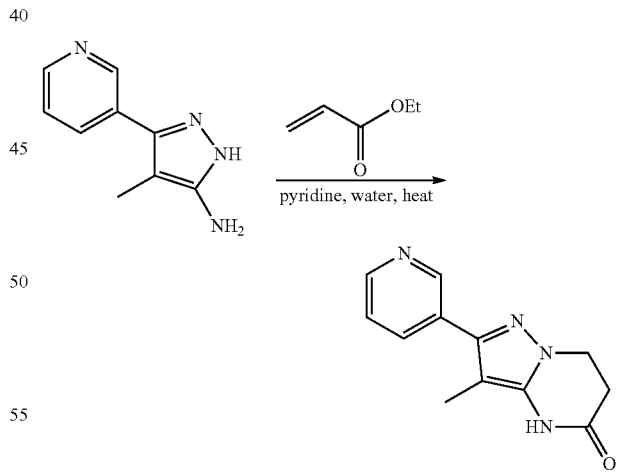

Ethyl acrylate (0.5 mL) was added to a solution of 4-methyl-3-(pyridin-3-yl)-1H-pyrazol-5-amine (300 mg, 1.72 mmol) in pyridine (4 mL) and water (1 mL) and the resulting mixture heated to reflux overnight. After cooling to rt, the solvent was removed in vacuo and the residue re-crystallized from MeOH to give the desired product: MS (m/z): 229.1 [M+H]+, 1HNMR (400 MHz, CD3OD) δ 8.80 (d, 1 H, J=1.2 Hz), 8.53 (dd, 1 H, J=1.2 Hz, J=4.8 Hz), 8.07-8.09 (m, 1 H), 7.52 (dd, 1 H, J=4.8 Hz, J=8.0 Hz), 4.36 (t, 2 H, J=7.2 Hz), 2.94 (t, 2 H, J=7.2 Hz), 2.13 (s, 3 H).

Step D. 3,4-dimethyl-2-(pyridin-3-yl)-6,7-dihydro-pyrazolo[1,5-a]pyrimidin-5(4H)-one

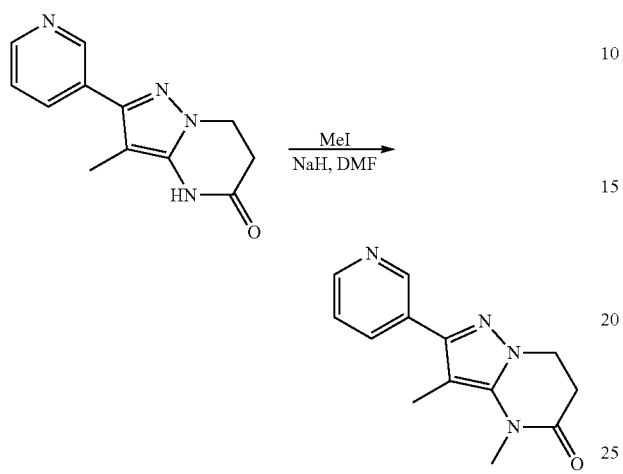

To a solution of 3-methyl-2-(pyridine-3-yl)-6,7-dihydro-pyrazolo[1,5-a]pyrimidin-5(4H)-one (50 mg, 0.22 mmol) in DMF (5 mL) was added NaH (13 mg, 0.33 mmol). The resulting mixture was stirred at room temperature for 30 minutes, and then iodomethane (47 mg, 0.33 mmol) was added and stirred at room temperature for 30 minutes. The mixture was quenched with water (20 mL) and extracted with ethyl acetate (10 mL×2). The combined organic layers were dried, filtered, concentrated in vacuo and re-crystallized from MeOH to give 3,4-dimethyl-2-(pyridine-3-yl)-6,7-dihydro-pyrazolo[1,5-a]pyrimidin-5(4 H)-one: MS (m/z): 243.1 [M+H]$^+$, $^1$HNMR (400 MHz, CD$_3$OD) δ 8.74 (s, 1H), 8.55 (d, 1 H, J=4.0 Hz), 8.03 (d, 1 H, J=8.0 Hz), 7.54 (dd, 1 H, J=4.8 Hz, J=8.0 Hz), 4.35 (t, 2H, J=6.8 Hz), 3.50 (s, 3 H), 2.95 (t, 2 H, J=6.8 Hz), 2.30 (s, 3H).

The compounds in Table 2 were all prepared using chemistry described in Example 7.

TABLE 2

| Example | Structure | Name | LCMS |
|---|---|---|---|
| 7 | | 3-methyl-2-(5-methylpyridin-3-yl)-6,7-dihydropyrazolo[1,5-a]pyrimidin-5(4H)-one | 243.1 |
| 8 | | 3,4-dimethyl-2-(5-methylpyridin-3-yl)-6,7-dihydropyrazolo[1,5-a]pyrimidin-5(4H)-one | 257.1 |
| 9 | | 3-ethyl-4-methyl-2-(5-methylpyridin-3-yl)-6,7-dihydropyrazolo[1,5-a]pyrimidin-5(4H)-one | 271.1 |
| 10 | 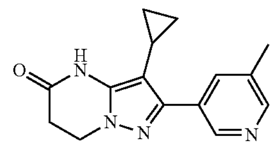 | 3-cyclopropyl-2-(5-methylpyridin-3-yl)-6,7-dihydropyrazolo[1,5-a]pyrimidin-5(4H)-one | 269.1 |
| 11 | 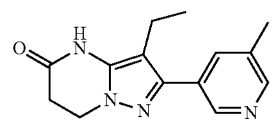 [SMILES: CCc1c(-c2cncc(C)c2)nn2c1NC(=O)CC2] | 3-ethyl-2-(5-methylpyridin-3-yl)-6,7-dihydropyrazolo[1,5-a]pyrimidin-5(4H)-one | 257.1 |
| 12 | 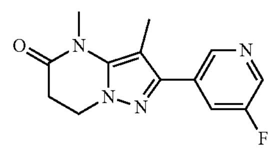 [SMILES: Cc1c(-c2cncc(F)c2)nn2c1N(C)C(=O)CC2] | 2-(5-fluoropyridin-3-yl)-3,4-dimethyl-6,7-dihydropyrazolo[1,5-a]pyrimidin-5(4H)-one | 261.1 |
| 13 | 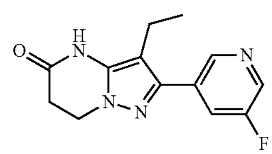 [SMILES: CCc1c(-c2cncc(F)c2)nn2c1NC(=O)CC2] | 3-ethyl-2-(5-fluoropyridin-3-yl)-6,7-dihydropyrazolo[1,5-a]pyrimidin-5(4H)-one | 261.1 |
| 14 | 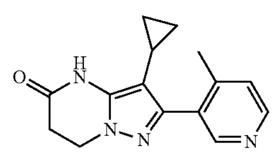 [SMILES: Cc1ccncc1-c1nn2c(c1C1CC1)NC(=O)CC2] | 3-cyclopropyl-2-(4-methylpyridin-3-yl)-6,7-dihydropyrazolo[1,5-a]pyrimidin-5(4H)-one | 269.1 |
| 15 | 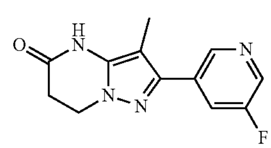 [SMILES: Cc1c(-c2cncc(F)c2)nn2c1NC(=O)CC2] | 2-(5-fluoropyridin-3-yl)-3-methyl-6,7-dihydropyrazolo[1,5-a]pyrimidin-5(4H)-one | 247.1 |
| 16 | 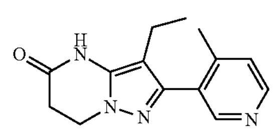 | 3-ethyl-2-(4-methylpyridin-3-yl)-6,7-dihydropyrazolo[1,5-a]pyrimidin-5(4H)-one | 257.1 |
| 17 | 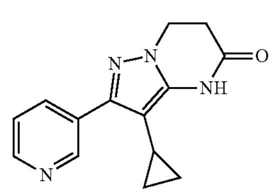 [SMILES: O=C1CCn2nc(-c3cccnc3)c(C3CC3)c2N1] | 3-cyclopropyl-2-pyridin-3-yl-6,7-dihydropyrazolo[1,5-a]pyrimidin-5(4H)-one | 255.1 |
| 18 | 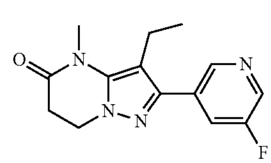 [SMILES: CCc1c(-c2cncc(F)c2)nn2c1N(C)C(=O)CC2] | 3-ethyl-2-(5-fluoropyridin-3-yl)-4-methyl-6,7-dihydropyrazolo[1,5-a]pyrimidin-5(4H)-one | 275.1 |

TABLE 2-continued

| Example | Structure | Name | LCMS |
|---|---|---|---|
| 19 | 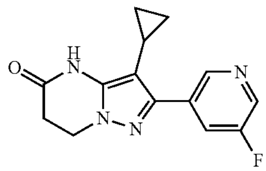 [SMILES: O=C1CCn2nc(-c3cncc(F)c3)c(C3CC3)c2N1] | 3-cyclopropyl-2-(5-fluoropyridin-3-yl)-6,7-dihydropyrazolo[1,5-a]pyrimidin-5(4H)-one | 273.1 |
| 20 | 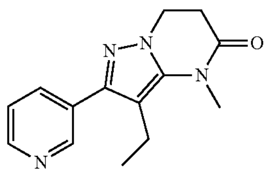 [SMILES: CCc1c(-c2cccnc2)nn2c1N(C)C(=O)CC2] | 3-ethyl-4-methyl-2-pyridin-3-yl-6,7-dihydropyrazolo[1,5-a]pyrimidin-5(4H)-one | 257.1 |
| 21 | 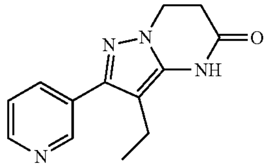 [SMILES: CCc1c(-c2cccnc2)nn2c1NC(=O)CC2] | 3-ethyl-2-pyridin-3-yl-6,7-dihydropyrazolo[1,5-a]pyrimidin-5(4H)-one | 243.1 |
| 22 | 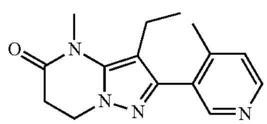 [SMILES: CCc1c(-c2cnccc2C)nn2c1N(C)C(=O)CC2] | 3-ethyl-4-methyl-2-(4-methylpyridin-3-yl)-6,7-dihydropyrazolo[1,5-a]pyrimidin-5(4H)-one | 271.1 |
| 23 | 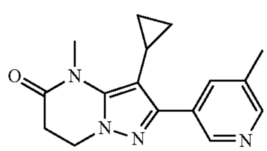 [SMILES: Cc1cncc(-c2nn3c(c2C2CC2)N(C)C(=O)CC3)c1] | 3-cyclopropyl-4-methyl-2-(5-methylpyridin-3-yl)-6,7-dihydropyrazolo[1,5-a]pyrimidin-5(4H)-one | 283.1 |

EXAMPLE 24

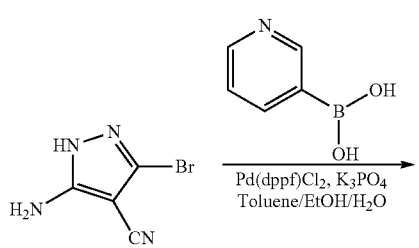

Step A. 5-amino-3-(pyridine-3-yl-1H-pyrazole-4-carbonitrile

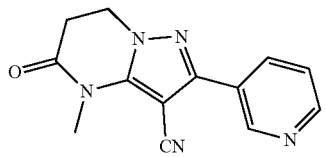 [SMILES: CN1C(=O)CCn2nc(-c3cccnc3)c(C#N)c21]

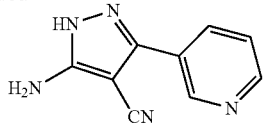

To a solution of 5-amino-3-bromo-1H-pyrazole-4-carbonitrile (500 mg, 2.67 mmol) in EtOH (5 mL)/H₂O (5 mL)/toluene (5 mL) were added 3-pyridine boronic acid (493 mg, 4.01 mmol), K₃PO₄ (2.13 g, 8.02 mmol) and Pd(dppf)Cl₂ (391 mg, 0.53 mmol) under N₂. The resulting mixture was stirred at 110° C. for 64 hours under N₂. After cooling to rt, the mixture was concentrated in vacuo, diluted with ethyl acetate, washed with water (10 mL×3) and dried over MgSO₄. After filtration, the filtrate was concentrated in vacuo. The residue was purified by preparative-TLC to afford 300 mg of the desired product: MS (m/z): 185.9 [M+H]+.

Step B. ethyl 3-(5-amino-4-cyano-3-(pyridine-3-yl)-1H-pyrazol-1-yl)propanoate

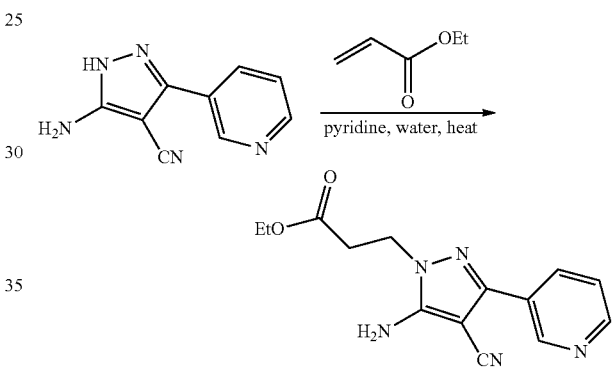

To a solution of 5-amino-3-(pyridine-3-yl)-1H-pyrazole-4-carbonitrile (300 mg, 1.62 mmol) in pyridine (4 mL)/H₂O (1 mL) was added ethyl acrylate (325 mg, 3.24 mmol). The resulting mixture was stirred at 100° C. for 5 hours. After cooling to rt, the mixture was concentrated in vacuo. The residue was purified by preparative-TLC to afford the desired product: MS (m/z): 286.0 [M+H]+.

Step C. 5-oxo-2-(pyridine-3-yl)-4,5,6,7-tetrahydropyrazolo[1,5-a]pyrimidine-3-carbonitrile

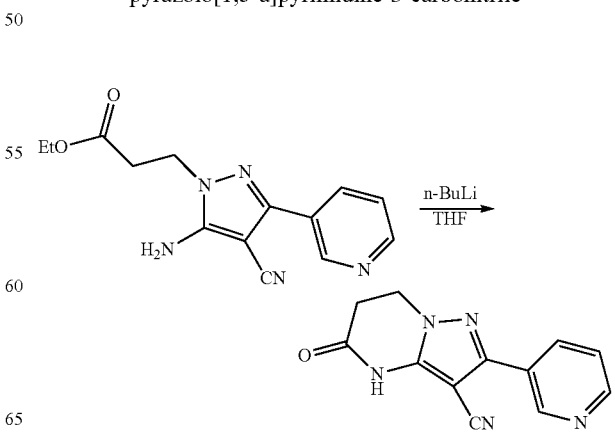

To a solution of ethyl 3-(5-amino-4-cyano-3-(pyridine-3-yl)-1H-pyrazol-1-yl)propanoate (213 mg, 0.75 mmol) in THF (5 mL) was added n-BuLi (0.6 mL, 1.49 mmol) at −60° C. The resulting mixture was stirred at −60° C. for 3 hours. 2 mL of water was added to quench the reaction and the THF was removed in vacuo. The residue was purified by HPLC to afford the desired product: MS (m/z): 240.1 [M+H]+, $^1$H NMR (DMSO, 400 MHz): δ11.79 (s, 1 H), 8.99 (s, 1 H), 8.65 (d, 1 H, J=5.2 Hz), 8.17 (d, 1 H, J=8.4 Hz), 7.57 (dd, 1 H, J=8.4 Hz, J=5.2 Hz), 4.38 (t, 2 H, J=7.6 Hz), 2.89 (t, 2 H, J=7.6 Hz).

Step D. 4-methyl-5-oxo-2-(pyridin-3-yl)-4,5,6,7-tetrahydropyrazolo[1,5-a]pyrimidine-3-carbonitrile

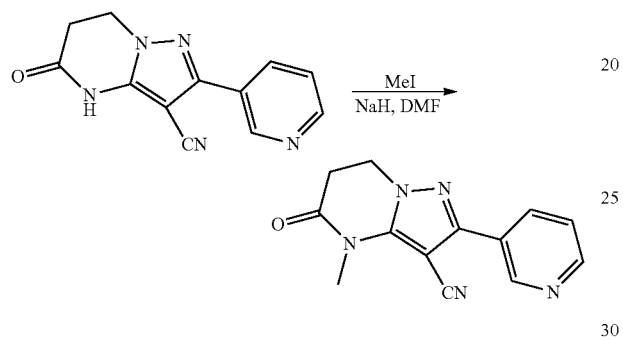

To a solution of 5-oxo-2-(pyridin-3-yl)-4,5,6,7-tetrahydropyrazolo[1,5-a]pyrimidine-3-carbonitrile (50 mg, 0.21 mmol) in DMF (2 mL) was added NaH (17 mg, 0.42 mmol) at 0° C. The resulting mixture was stirred at 0° C. for 30 mins, then methyl iodide (30 mg, 0.21 mmol) was added. The mixture was stirred at 0° C. for an additional 30 mins. 1 mL of water was added to quench the reaction which was extracted with ethyl acetate. The combined organic extracts were dried, filtered and concentrated in vacuo. The residue was purified by HPLC to afford 4-methyl-5-oxo-2-(pyridine-3-yl)-4,5,6,7-tetrahydropyrazolo[1,5-a]pyrimidine-3-carbonitrile: MS (m/z): 254.1 [M+H]+, $^1$H NMR (CD$_3$OD, 400 MHz): δ8.06 (s, 1 H), 8.60 (d, 1 H, J=1.6 Hz), 8.36 (d, 1H, J=8.0 Hz), 7.59 (dd, 1 H, J=8.0 Hz, J=56 Hz), 4.44 (t, 2 H, J=7.6 Hz), 3.04 (t, 2H, J=7.6 Hz).

The compounds in Table 3 were all prepared using chemistry described in Example 24.

TABLE 3

| Example | Structure | Name | LCMS |
|---|---|---|---|
| 25 | 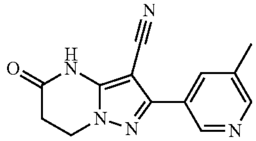 [SMILES: Cc1cncc(-c2nn3c(c2C#N)NC(=O)CC3)c1] | 2-(5-methylpyridin-3-yl)-5-oxo-4,5,6,7-tetrahydropyrazolo[1,5-a]pyrimidine-3-carbonitrile | 254.1 |
| 26 | 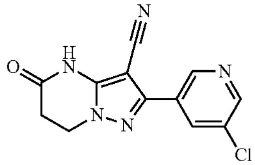 [SMILES: N#Cc1c(-c2cncc(Cl)c2)nn2c1NC(=O)CC2] | 2-(5-chloropyridin-3-yl)-5-oxo-4,5,6,7-tetrahydropyrazolo[1,5-a]pyrimidine-3-carbonitrile | 274.0 |

EXAMPLE 27

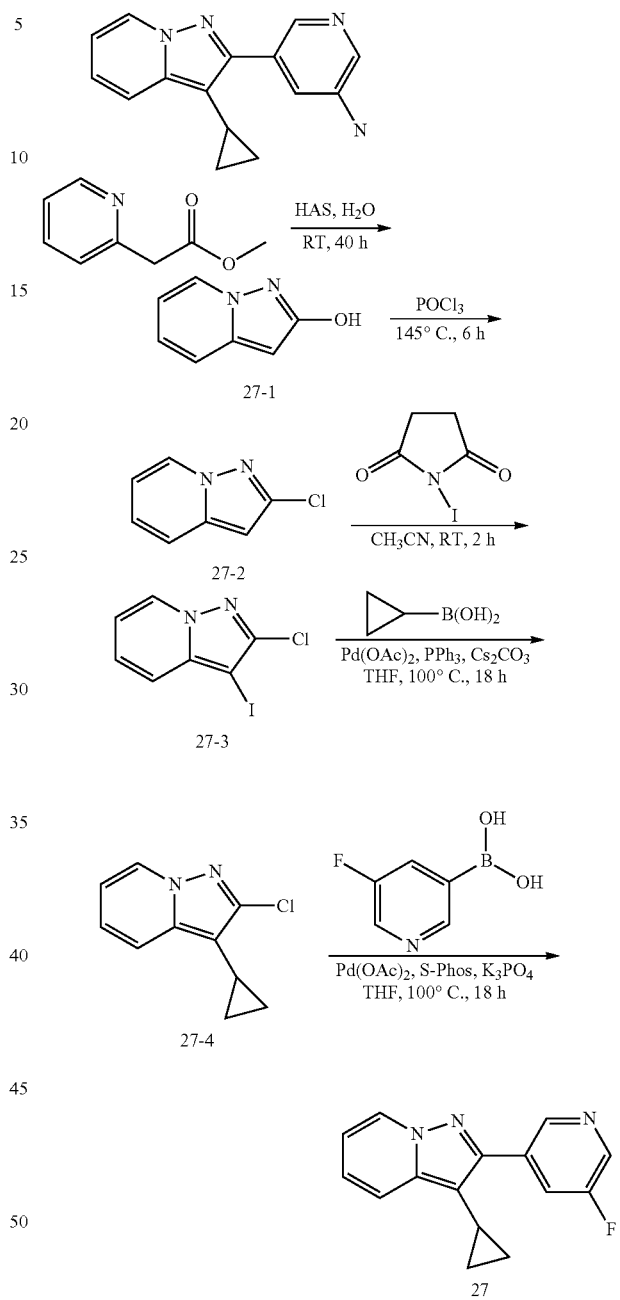

Step A. pyrazolo[1,5-a]pyridin-2-ol

Hydroxylamine-O-sulphonic acid (0.6 g, 0.0053 mol) was added to a stirred solution of methyl 2-(pyridin-2-yl) acetate (3.0 g, 0.019 mol) in water (3.0 mL) and the resulting mixture was allowed to stir at room temperature for 40 h. The reaction mixture was diluted with water (15 mL) and extracted with dichloromethane (3×20 mL). The combined organic layers were basified with 10% Na$_2$CO$_3$ solution. Aqueous layer was separated and extracted with dichloromethane (2×20 mL). Both the organic layers were combined and concentrated to recover the unreacted starting material. The aqueous portion was acidified with acetic acid (pH 5.0) and extracted with dichloromethane (3×20 mL). The combined organic layers were dried over sodium sulphate and concentrated under vacuum to obtain pyrazolo[1,5-a]pyridin-2-ol ($^1$H NMR (400 MHz, DMSO) δ 10.41 (bs, 1 H), 8.32-8.30 (d, J=6.8 Hz, 1 H), 7.34-7.32 (d, J=8.8 Hz, 1 H), 7.08-7.04 (t, J=7.6 Hz, 1 H), 6.63-6.56 (m, 1 H), 5.71 (s, 1 H).

Step B. 2-chloropyrazolo[1,5-a]pyridine

A stirred solution of pyrazolo[1,5-a]pyridin-2-ol (27-1; 0.9 g, 0.0067 mol) in POCl$_3$ (10 mL) was heated in a sealed tube at 145° C. for 6 h. The reaction mixture was cooled to room temperature, poured into ice cold water (20 mL) and extracted with dichloromethane (3×20 mL). The combined organic layers were washed with saturated sodium chloride, dried over sodium sulphate and concentrated under vacuum to afford the crude compound, which was purified by column chromatography to obtain the title compound. $^1$H NMR (400 MHz, DMSO-d$_6$) δ 8.36-8.34 (d, J=7.2 Hz, 1 H), 7.44-7.42 (d, J=9.2 Hz, 1 H), 7.17-7.13 (m, 1 H), 6.78-6.74 (m, 1 H), 6.43 (s, 1 H). MS (M+1): 152.8.

Step C. 2-chloro-3-iodopyrazolo-[1,5-a]pyridine

N-iodosuccinimide (1.06 g, 4.74 mmol) was added to a solution of 2-chloro-pyrazolo-[1,5-a]pyridine (27-2; 0.6 g, 3.95 mmol) in acetonitrile (18.0 mL). The resulting mixture was stirred at room temperature for 2 h and then concentrated under reduced pressure. The resulting residue was diluted with dichloromethane, washed with saturated aqueous sodium chloride solution, dried over magnesium sulphate, filtered and concentrated under reduced pressure. Purification by silica gel flash chromatography (5-10% ethyl acetate in hexanes) provided the title compound. $^1$H NMR (400 MHz, CDCl$_3$) δ 8.36-8.34 (d, J=6.8 Hz, 1 H), 7.40-7.37 (d, J=8.8 Hz, 1 H), 7.26-7.23 (m, 1 H), 6.84-6.81 (m, 1 H). MS (M+1): 279.0.

Step D.
2-chloro-3-cyclopropylpyrazolo[1,5-a]pyridine

A mixture 2-chloro-3-iodopyrazolo-[1,5-a]pyridine (27-3; 0.7 g, 2.52 mmol), cyclopropyl boronic acid (0.43 g, 5.036 mmol), and cesium carbonate (2.46 g, 7.56 mmol), in tetrahydrofuran (15.0 mL) was degassed for 10 min. Then triphenylphosphine (0.132 g, 0.504 mmol) and palladium acetate (0.056 g, 0.252 mmol) were added and heated in a sealed tube at 100° C. for 18 h. The reaction mixture was then cooled to room temperature, filtered and concentrated under reduced pressure. Purification of the resulting residue by flash chromatography on silica gel (0-5% ethyl acetate in hexanes) provided 2-chloro-3-cyclopropylpyrazolo[1,5-a]pyridine. $^1$H NMR (400 MHz, CDCl$_3$) δ 8.29-8.27 (d, J=7.2 Hz, 1 H), 7.50-7.48 (d, J=8.8 Hz, 1 H), 7.11-7.07 (t, J=7.8 Hz, 1 H), 6.72-6.69 (m, 1 H), 1.80-1.73 (m, 1 H), 0.98-0.95 (m, 2 H), 0.75-0.73 (m, 2 H). MS (M+1): 139.1.

Step E. (3-cyclopropyl-2-(5-fluoropyridin-3-yl) pyrazolo[1,5-a]pyridine

A solution of 2-chloro-3-cyclopropylpyrazolo-[1,5-a]pyridine (27-4; 0.2 g, 1.042 mmol), (5-fluoropyridin-3-yl)boronic acid (0.147 g, 1.042 mmol), and potassium phosphate tribasic (0.66 g, 3.126 mmol) in tetrahydrofuran (15 mL) was degassed for 10 min. Next 2-dicyclohexylphosphino-2',6'-dimethoxy-1,1'-biphenyl (0.085 g, 0.208 mmol) and palladium acetate (0.023 g, 0.104 mmol) were added and heated in a sealed tube at 100° C. for 18 h. The reaction mixture was then cooled to room temperature, filtered and concentrated under reduced pressure. Purification of the resulting residue by prep HPLC provided 3-cyclopropyl-2-(5-fluoropyridin-3-yl) pyrazolo[1,5-a]pyridine. $^1$H NMR (400 MHz, DMSO-d$_6$) δ 9.07 (s, 1 H), 8.67-8.65 (d, J=8.0 Hz, 1 H), 8.62-8.61 (d, J=2.4 Hz, 1 H), 8.19-8.17 (d, J=8.0 Hz, 1 H), 7.74-7.72 (d, J=8.0 Hz, 1 H), 7.26-7.22 (t, J=8.0 Hz, 1 H), 6.93-6.90 (t, J=8.0 Hz, 1 H), 2.10-2.05 (m, 1 H), 1.02-1.01 (d, J=4.0 Hz, 2 H), 0.43-0.42 (d, J=4.0 Hz, 2 H), MS (M+1): 254.1.

The compounds in Table 4 were prepared using the chemistry described above in Example 27.

TABLE 4

| Example | Structure | Name | LCMS (M + 1) |
| --- | --- | --- | --- |
| 28 | 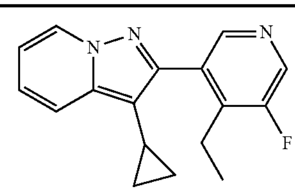 | 3-cyclopropyl-2-(4-ethyl-5-fluoropyridin-3-yl)pyrazolo[1,5-a]pyridine | 282.3 |
| 29 | 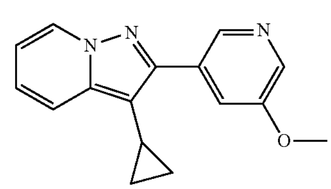 [SMILES: COc1cncc(-c2nn3ccccc3c2C2CC2)c1] | 3-cyclopropyl-2-(5-methoxypyridin-3-yl)pyrazolo[1,5-a]pyridine | 266.3 |

TABLE 4-continued

| Example | Structure | Name | LCMS (M + 1) |
|---|---|---|---|
| 30 | 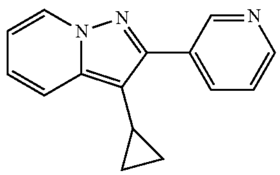 [SMILES: c1cncc(-c2nn3ccccc3c2C2CC2)c1] | 3-cyclopropyl-2-(pyridin-3-yl)pyrazolo[1,5-a]pyridine | 236.2 |
| 31 | 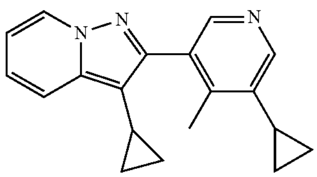 [SMILES: Cc1c(-c2nn3ccccc3c2C2CC2)cncc1C1CC1] | 3-cyclopropyl-2-(5-cyclopropyl-4-methylpyridin-3-yl)pyrazolo[1,5-a]pyridine | 290.3 |
| 32 | 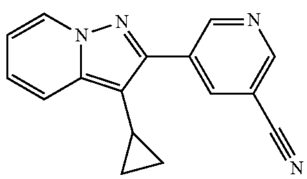 [SMILES: N#Cc1cncc(-c2nn3ccccc3c2C2CC2)c1] | 5-(3-cyclopropylpyrazolo[1,5-a]pyridin-2-yl)nicotinonitrile | 261.2 |
| 33 | 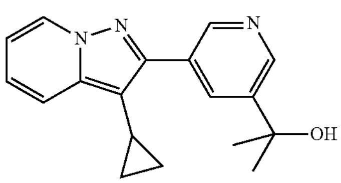 [SMILES: CC(C)(O)c1cncc(-c2nn3ccccc3c2C2CC2)c1] | 2-(5-(3-cyclopropylpyrazolo[1,5-a]pyridin-2-yl)pyridin-3-yl)propan-2-ol | 294.3 |
| 34 | 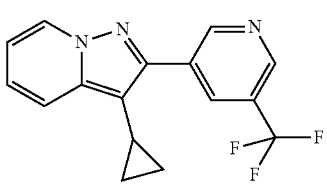 [SMILES: FC(F)(F)c1cncc(-c2nn3ccccc3c2C2CC2)c1] | 3-cyclopropyl-2-(5-(trifluoromethyl)pyridin-3-yl)pyrazolo[1,5-a]pyridine | 304.2 |
| 35 | 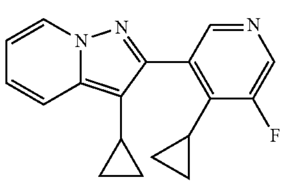 [SMILES: Fc1cncc(-c2nn3ccccc3c2C2CC2)c1C1CC1] | 3-cyclopropyl-2-(4-cyclopropyl-5-fluoropyridin-3-yl)pyrazolo[1,5-a]pyridine | 294.3 |
| 36 | 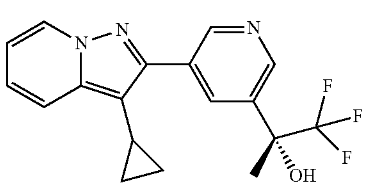 [SMILES: C[C@@](O)(c1cncc(-c2nn3ccccc3c2C2CC2)c1)C(F)(F)F] | (R)-2-(5-(3-cyclopropylpyrazolo[1,5-a]pyridin-2-yl)pyridin-3-yl)-1,1,1-trifluoropropan-2-ol | 348.1 |

EXAMPLE 37

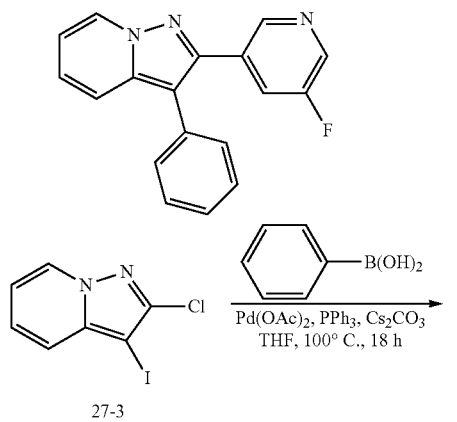

27-3

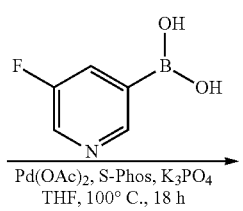

37-1

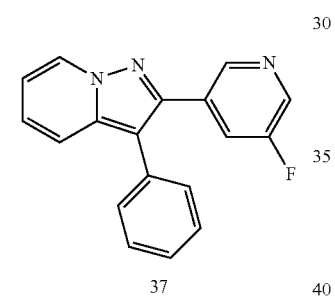

37

Step A. 2-chloro-3-phenylpyrazolo[1,5-a]pyridine

A mixture 2-chloro-3-iodopyrazolo[1,5-a]pyridine (27-3; 0.8 g, 2.87 mmol), phenyl boronic acid (0.42 g, 3.44 mmol), and cesium carbonate (2.8 g, 8.61 mmol), in tetrahydrofuran (15.0 mL) was degassed for 10 min. Next, triphenylphosphine (0.15 g, 0.574 mmol) and palladium acetate (0.064 g, 0.287 mmol) were added and heated in a sealed tube at 100° C. for 18 h. The reaction mixture was then cooled to room temperature, filtered and concentrated under reduced pressure. Purification of the resulting residue by flash chromatography on silica gel (0-5% ethyl acetate in hexanes) provided 2-chloro-3-phenylpyrazolo[1,5-a]pyridine. $^1$H NMR (400 MHz, DMSO-$d_6$) δ 8.70-8.68 (d, J=7.2 Hz, 1 H), 7.69-7.67 (d, J=8.8 Hz, 1 H), 7.57-7.55 (d, J=7.2 Hz, 2 H), 7.52-7.48 (t, J=7.6 Hz, 2 H), 7.39-7.34 (m, 2 H), 7.03-7.00 (m, 1 H). MS (M+1): 229.1.

Step B. 2-(5-fluoropyridin-3-yl)-3-phenylpyrazolo[1,5-a]pyridine

A solution of 2-chloro-3-phenylpyrazolo[1,5-a]pyridine (37-1; 0.2 g, 0.88 mmol), (5-fluoropyridin-3-yl)boronic acid (0.15 g, 1.05 mmol), and potassium phosphate tribasic (0.66 g, 2.64 mmol) in tetrahydrofuran (10 mL) was degassed for 10 min. Then 2-dicyclohexylphosphino-2',6'-dimethoxy-1,1'-biphenyl (0.065 g, 0.16 mmol) and palladium acetate (0.02 g, 0.08 mmol) were added and heated in a sealed tube at 100° C. for 18 h. The reaction mixture was then cooled to room temperature, filtered and concentrated under reduced pressure. Purification of the resulting residue by prep HPLC (Analytical Conditions: Column: Xbridge C18 (250 mm×4.6 mm×5 m), Mobile phase (A): water, Mobile phase (B): Acetonitrile, Flow rate: 1.0 mL/min, GradientT/% B:0/20, 8/50, 25/50, 27/20, 30/20) provided 2-(5-fluoropyridin-3-yl)-3-phenylpyrazolo[1,5-a]pyridine. $^1$H NMR (400 MHz, DMSO-$d_6$) δ 8.81-8.79 (d, J=8.0 Hz, 1 H), 8.57-8.56 (d, J=4.0 Hz, 2 H), 7.76-7.73 (d, J=12.0 Hz, 1 H), 7.61-7.59 (d, J=8.0 Hz, 1 H), 7.49-7.45 (m, 1 H). MS (M+1): 290.1.

EXAMPLE 38

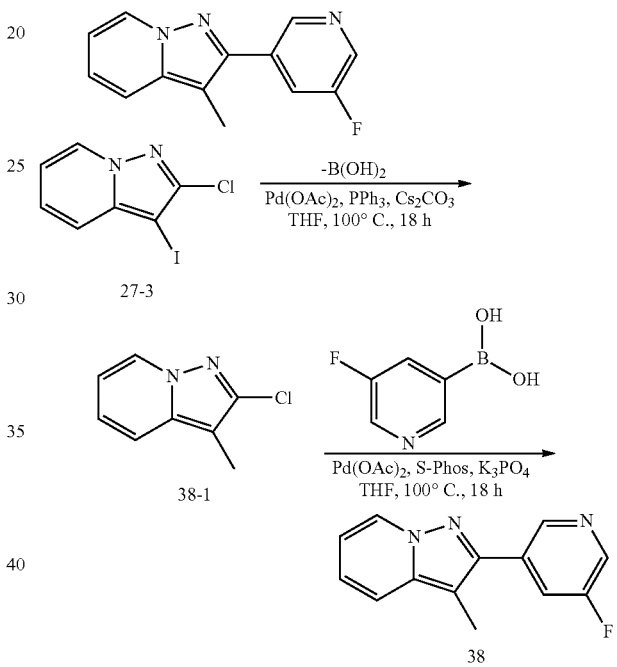

Step A. 2-chloro-3-methylpyrazolo[1,5-a]pyridine

A mixture of 2-chloro-3-iodopyrazolo[1,5-a]pyridine (27-3; 0.8 g, 2.87 mmol), methyl boronic acid (0.345 g, 5.7 mmol), and cesium carbonate (2.8 g, 8.61 mmol) in tetrahydrofuran (15 mL) was degassed for 10 min. Then triphenylphosphine (0.15 g, 0.574 mmol) and palladium acetate (0.064 g, 0.287 mmol) were added and heated in a sealed tube at 100° C. for 18 h. The reaction mixture was then cooled to room temperature, filtered and concentrated under reduced pressure. Purification of the resulting residue by flash chromatography on silica gel (0-5% ethyl acetate in hexanes) provided 2-chloro-3-methylpyrazolo[1,5-a]pyridine. $^1$H NMR (400 MHz, DMSO-$d_6$) δ 8.55-8.53 (d, J=8 Hz, 1 H), 7.61-7.59 (d, J=8 Hz, 1 H), 7.25-7.21 (t, J=8 Hz, 1 H), 6.89-6.86 (t, J=8 Hz, 1 H), 2.19 (s, 3 H). MS (M+1): 167.1.

Step B. 2-(5-fluoropyridin-3-yl)-3-methylpyrazolo[1,5-a]pyridine

A solution 2-chloro-3-methylpyrazolo[1,5-a]pyridine (38-1; 0.15 g, 0.9 mmol), (5-fluoropyridin-3-yl)boronic acid (0.15 g, 1.05 mmol), and potassium phosphate tribasic (0.574 g, 2.7 mmol) in tetrahydrofuran (10 mL) was degassed for 10 min. Then 2-dicyclohexylphosphino-2',6'-dimethoxy-1,1'-biphenyl (0.074 g, 0.18 mmol) and palladium acetate (0.02 g, 0.09 mmol) were added and heated in a sealed tube at 100° C. for 18 h. The reaction mixture was then cooled to room temperature, filtered and concentrated under reduced pressure. Purification of the resulting residue by prep HPLC (Analytical Conditions: Column: XTERRA C18 (250 mm×4.6 mm×5 µm) mobile phase(A):0.01% ammonia in water, mobile phase (B): acetonitrile flow rate: 1.0 mL/min time/% B: 0/20, 8/50, 25/50, 26/20, 30/20) provided 2-(5-fluoropyridin-3-yl)-3-methylpyrazolo[1,5-a]pyridine. $^1$H NMR (400 MHz, DMSO-$d_6$) δ 8.88 (s, 1 H), 8.67-8.65 (d, J=8.0 Hz, 1 H), 8.06-8.03 (d, J=12 Hz, 1 H), 7.73-7.71 (d, J=8.0 Hz, 1 H), 7.23-7.20 (t, J=4.0 Hz, 1 H), 6.92-6.89 (t, J=4.0 Hz, 1 H), 2.45 (s, 3 H). MS (M+1): 228.0.

Example 39 was prepared following the synthetic procedure as described above.

TABLE 2

| Example | Structure | IUPAC Name | LCMS (M + 1) |
|---|---|---|---|
| 39 | 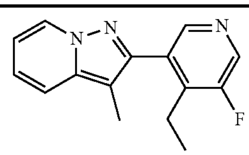 | 2-(4-ethyl-5-fluoropyridin-3-yl)-3-methylpyrazolo[1,5-a]pyridine | 256.1 |

Assay Description and Results

Methods for V79-Human-CYP11B2 and V79-Human-CYP11B1 Assays: V79 cell lines stably expressing the either the human CYP11B2 or the human CYP11B1 enzyme were generated using a standard transfection protocol. V79 cells were transfected with plasmids pTriEx3-Hygro-hCyp11B2 or pTriEx3-Hygro-hCyp11B1 using Lipofectamine2000 reagent. V79 cells that stably express the human CYP11B2 or human CYP11B1 enzyme were selected for and maintained in DMEM supplemented with 10% FBS and 400 µg/mL hygromycin for ~2 weeks. Single cell clones were generated by infinite dilution in DMEM supplemented with 10% FBS and 400 µg/mL hygromycin until single colonies were obtained. Clones V79-hCYP11B2-CLE9 and V79-hCYP11B1-8CLC7, were determined to produce the most aldosterone and cortisol, respectively, and were selected for inhibitor screening. For testing of inhibitors, cells were harvested at 80% confluency with 0.5% Trypsan-EDTA, washed once in PBS, and reconstituted in DMEM+0.1% BSA media at a cell concentration of 600,000 cells/mL for the CYP11B2 assay and 280,000 cells/mL for the CYP11B1 assay. 25 µL of cells were added to a 384 well tissue culture treated plate and mixed with 0.3 µL of inhibitor or DMSO (1% final DMSO concentration) for 1 hour at 37° C., 5% $CO_2$. After pre-incubation with inhibitor, the reaction was initiated by adding 5 µL of substrate (final concentration of 125 nM 11-deoxy-corticosterone for the CYP11B2 assay or 250 nM 11-deoxy-cortisol for the CYP11B1 assay). The reaction was carried out for 3 hours at 37° C., 5% $CO_2$ and was stopped by harvesting the supernatants. The amount of product in the supernatant (aldosterone for CYP11B2 assay and cortisol for the CYP11B1 assay) was measured using HTRF-based assay kit (Aldosterone HTRF-CisBio#64ALDPEB, Cortisol HTRF-CisBio #63IDC002-CORT). $IC_{50}$s for the inhibitor were determined by plotting the amount of product formed against the concentration of inhibitor using sigmoidal dose-response curve (variable slope) fit in GraphPad.

The compounds of Examples 1-39 were tested in the V79-Human-CYP11B2 cell assay and found to have $IC_{50}$s for inhibition of human CYP11B2 of less than 10000 nM. A sub-group of compounds had $IC_{50}$s less than or equal to 250 nM, and a further sub-group of compounds had $IC_{50}$s less than or equal to 50 nM.

The compounds of Examples 1-39 were also tested in the V79-Human-CYP11B1 cell assay. A sub-group of compounds were at least 10-fold more selective for inhibition of CYP11B2 as compared to CYP11B1, and a further sub-group of compounds were at least 30-fold more selective for inhibition of CYP11B2. Representative examples of data collected for compounds of the present invention are shown in Table 4 below Table 4

TABLE 4

| Example | IUPAC Name | V79 Human CYP11B2 $IC_{50}$ (nM) | V79 Human CYP11B1 $IC_{50}$ (nM) |
|---|---|---|---|
| 7 | 3-methyl-2-(5-methylpyridin-3-yl)-6,7-dihydropyrazolo[1,5-a]pyrimidin-5(4H)-one | 2.2 | 282 |
| 8 | 3,4-dimethyl-2-(5-methylpyridin-3-yl)-6,7-dihydropyrazolo[1,5-a]pyrimidin-5(4H)-one | 9.8 | 3715 |
| 9 | 3-ethyl-4-methyl-2-(5-methylpyridin-3-yl)-6,7-dihydropyrazolo[1,5-a]pyrimidin-5(4H)-one | 7.8 | 2344 |
| 10 | 3-cyclopropyl-2-(5-methylpyridin-3-yl)-6,7-dihydropyrazolo[1,5-a]pyrimidin-5(4H)-one | 13.2 | 71%* |
| 12 | 2-(5-fluoropyridin-3-yl)-3,4-dimethyl-6,7-dihydropyrazolo [1,5-a]pyrimidin-5(4H)-one | 19.1 | 1820 |
| 13 | 3-ethyl-2-(5-fluoropyridin-3-yl)-6,7-dihydropyrazolo[1,5-a]pyrimidin-5(4H)-one | 11.7 | 1349 |
| 15 | 2-(5-fluoropyridin-3-yl)-3-methyl-6,7-dihydropyrazolo [1,5-a]pyrimidin-5(4H)-one | 30.9 | 3631 |
| 19 | 3-cyclopropyl-2-(5-fluoropyridin-3-yl)-6,7-dihydropyrazolo[1,5-a]pyrimidin-5(4H)-one | 102.3 | 38%* |
| 25 | 2-(5-methylpyridin-3-yl)-5-oxo-4,5,6,7-tetrahydropyrazolo[1,5-a]pyrimidine-3-carbonitrile | 61%** | |
| 26 | 2-(5-chloropyridin-3-yl)-5-oxo-4,5,6,7-tetrahydropyrazolo[1,5-a]pyrimidine-3-carbonitrile | 51%** | 1072 |

*= % inhibition at 10 µM
**= % inhibition at 1 µM

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:

1. A compound of the structural formula

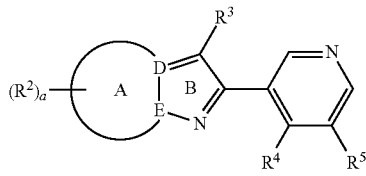

I or a pharmaceutically acceptable salt thereof
wherein:
Ring A is attached to Ring B via positions D and E and is:

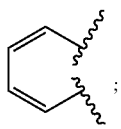

D is C;
E is N;
$R^2$ is halogen; —CN; —$OR^7$; —$N(R^{10})C(O)R^7$; —$NR^{11}R^{12}$; —$C(O)R^7$; —$C(O)N(R^{11})(R^{12})$; —$C(O)OR^7$; —$SO_2N(R^{10})$—$R^7$; —$N(R^{10})SO_2$—$R^7$; alkyl optionally substituted one or more times by halogen, —$OR^7$, $NR^8R^9$, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; heterocycloalkyl optionally substituted one or more times by halogen, alkyl, haloalkyl, —$OR^7$, —CN, —$NR^8R^9$—$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; aryl optionally substituted one or more times by halogen, alkyl, haloalkyl, cycloalkyl, —$OR^7$, —CN, —$NR^8R^9$—$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; or heteroaryl optionally substituted one or more times (e.g., 1 to 4 times) by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$;
$R^3$ is H; halogen; —CN; alkyl optionally substituted one or more times by halogen or cycloalkyl optionally substituted once or twice by alkyl or halogen; cycloalkyl optionally substituted once or twice by alkyl or halogen; aryl optionally substituted one or more times by halogen, alkyl, haloalkyl, cycloalkyl, —$OR^7$, —CN, —$NR^8R^9$, —$N(R^{10})C(O)(R^7)$, —$C(O)N(R^8)(R^9)$, —$C(O)OR^7$—$SO_2N(R^{10})$—$R^7$, —$N(R^{10})SO_2$—$R^7$, or —$S(O)_m$—$R^7$; or —$C(O)OR^7$;

$R^4$ is H; halogen; —CN; —$OR^7$; —$NR^8R^9$; —$N(R^{10})C(O)R^7$; —$C(O)N(R^8)(R^9)$; —$C(O)R^7$; —$C(O)OR^7$; —$SO_2N(R^{10})$—$R^7$; —$N(R^{10})S(O)_2$—$R^7$; —$S(O)_n$—$R^7$; alkyl optionally substituted one or more times by halogen, —$OR^7$, —$NR^8R^9$, —CN, —$N(R^{11})C(O)R^7$, —$C(O)N(R^8)(R^9)$, —$C(O)OR^7$, —$SO_2N(R^{10})$—$R^7$, —$N(R^{10})S(O)_2$—$R^7$, or —$S(O)_n$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^8$, —$SO_2N(R^{10})$—$R^7$, —$N(R^{10})SO_2$—$R^7$ or —$S(O)_m$—$R^7$; aryl optionally substituted one or more times by halogen, alkyl, haloalkyl, cycloalkyl, —$OR^7$, —CN, —$NR^8R^9$, —$N(R^{10})C(O)(R^7)$, —$C(O)N(R^8)(R^9)$, —$C(O)OR^7$—$SO_2N(R^{10})$—$R^7$, —$N(R^{10})SO_2$—$R^7$, or —$S(O)_m$—$R^7$; heterocycloalkyl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)OR^7$—$SO_2N(R^{10})$—$R^7$, —$N(R^{10})SO_2$—$R^7$ or —$S(O)_m$—$R^7$; or heteroaryl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$;

$R^5$ is halogen; —CN; —$OR^7$; —$NR^8R^9$; —$N(R^{10})C(O)R^7$; —$C(O)N(R^8)(R^9)$; —$C(O)R^7$; —$C(O)OR^7$; —$SO_2N(R^{10})$—$R^7$; —$N(R^{10})S(O)_2$—$R^7$; —$S(O)_n$—$R^7$; alkyl substituted one or more times by halogen, —$OR^7$, —$NR^8R^9$, —CN, —$N(R^{11})C(O)R^7$, —$C(O)N(R^8)(R^9)$, —$C(O)OR^7$, —$SO_2N(R^{10})$—$R^7$, —$N(R^{10})S(O)_2$—$R^7$, or —$S(O)_n$—$R^7$; cycloalkyl optionally substituted one or more times by halogen, alkyl, haloalkyl, —$OR^7$, —$NR^8R^9$, —CN, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; aryl optionally substituted one or more times by halogen, alkyl, haloalkyl, cycloalkyl, —$OR^7$, —CN, —$NR^8R^9$—$N(R^{10})C(O)(R^7)$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; heterocycloalkyl optionally substituted one or more times by halogen, alkyl, haloalkyl, cycloalkyl, —$OR^7$, —CN, —$NR^8R^9$—$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; or heteroaryl optionally substituted one or more times by halogen, alkyl, haloalkyl, cycloalkyl, —$OR^7$, —CN, —$NR^8R^9$, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$;

or $R^4$ and $R^5$ are joined together to form a 5-7 membered carbocyclic or heterocyclic ring that is fused to the pyridyl ring to which $R^4$ and $R^5$ are attached, wherein the ring formed by $R^4$ and $R^5$ is optionally substituted by 1 to 3 $R^6$;

$R^6$ is independently H; halogen; —CN; —$OR^7$; —$NR^8R^9$; —$N(R^{10})C(O)R^7$; —$C(O)N(R^7)(R^8)$; —$C(O)N(R^8)(R^9)$; —$C(O)OR^7$; —$SO_2N(R^{10})$—$R^7$; —$N(R^{10})SO_2$—$R^7$; —$S(O)_m$—$R^7$; alkyl optionally substituted one or more times by halogen, —$OR^7$, —$NR^8R^9$, —CN, —$N(R^{10})C(O)R^7$, —$C(O)N(R^8)(R^9)$, —$C(O)OR^7$, —$SO_2N(R^{10})$—$R^7$, —$N(R^{10})SO_2$—$R^7$ or —$S(O)_m$—$R^7$; cycloalkyl optionally substituted one or more times by halogen, alkyl, haloalkyl, —$OR^7$, —$NR^8R^9$, —CN, —N(R$^{10}$)C(O)R$^7$, —C(O)N(R$^8$)(R$^9$), —C(O)OR$^7$—SO$_2$N(R$^{10}$)—R$^7$, —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^7$ is independently H; alkyl optionally substituted one or more times by halogen, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; cycloalkyl optionally substituted one or more times by halogen, alkyl, haloalkyl, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OH, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; or heteroaryl optionally substituted one or more times by halogen, alkyl, haloalkyl, cycloalkyl, —OR$^{10}$, —NR$^8$R$^9$, —CN, —N(R$^9$)C(O)R$^{10}$, —C(O)N(R$^8$)(R$^9$), —C(O)OR$^{10}$ or —S(O)$_m$—R$^{10}$;

R$^8$ is independently H or alkyl;

R$^9$ is independently H or alkyl;

or R$^8$ and R$^9$ are joined together with the nitrogen to which they are attached form a saturated 5- to 7-membered heterocyclic ring;

R$^{10}$ is independently H or alkyl;

R$^{11}$ is independently H; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times by halogen, alkyl, haloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

R$^{12}$ is independently H; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

a is 0, 1, 2, 3 or 4;

n is 1 or 2; and m is 0, 1 or 2.

2. A compound as defined in claim 1 or a pharmaceutically acceptable salt thereof wherein:

R$^2$ is halogen; —CN; —OR$^7$; —N(R$^{10}$)C(O)R$^7$; —NR$^{11}$R$^{12}$; —C(O)R$^7$; —C(O)N(R$^{11}$)(R$^{12}$); —C(O)OR$^7$; —SO$_2$N(R$^{10}$)—R$^7$; —N(R$^{10}$)SO$_2$—R$^7$; alkyl optionally substituted one or more times by halogen, —OR$^7$, NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^3$ is H; halogen; —CN; alkyl optionally substituted one or more times by halogen or cycloalkyl optionally substituted once or twice by alkyl or halogen; cycloalkyl optionally substituted once or twice by alkyl or halogen; or —C(O)OR$^7$;

R$^4$ is H; halogen; —CN; —OR$^7$; —NR$^8$R$^9$; —N(R$^{10}$)C(O)R$^7$; —C(O)R$^7$; —C(O)N(R$^8$)(R$^9$); —C(O)OR$^7$; —SO$_2$N(R$^{10}$)—R$^7$; —N(R$^{10}$)S(O)$_2$—R$^7$; —S(O)$_n$—R$^7$; alkyl optionally substituted one or more times by halogen, —OR$^7$, —NR$^8$R$^9$, —CN, —SO$_2$N(R$^{10}$)—R$^7$, —N(R$^{10}$)C(O)R$^7$, —C(O)N(R$^8$)(R$^9$), —C(O)OR$^7$, —N(R$^{10}$)S(O)$_2$—R$^7$ or —S(O)$_n$R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^5$ is halogen; —CN; —OR$^7$; —NR$^8$R$^9$; —N(R$^{10}$)C(O)R$^7$; C(O)R$^7$; —C(O)N(R$^8$)(R$^9$); —C(O)OR$^7$; —SO$_2$N(R$^{10}$)—R$^7$; —N(R$^{10}$)S(O)$_2$—R$^7$; —S(O)$_n$—R$^7$; alkyl substituted one or more times by halogen, —OR$^7$, —NR$^8$R$^9$, —CN, —SO$_2$N(R$^{10}$)—R$^7$, —N(R$^{10}$)C(O)R$^7$, —C(O)N(R$^8$)(R$^9$), —C(O)OR$^7$, —N(R$^{10}$)S(O)$_2$—R$^7$, or —S(O)$_n$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$, —N(R$^{10}$)C(O)(R$^7$), —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

or R$^4$ and R$^5$ are joined together to form a 5-7 membered carbocyclic or heterocyclic ring that is fused to the pyridyl ring to which R$^4$ and R$^5$ are attached, wherein the ring formed by R$^4$ and R$^5$ is optionally substituted by 1 to 3 R$^6$;

R$^6$ is independently H; halogen; —CN; —OR$^7$; —NR$^8$R$^9$; —N(R$^{10}$)C(O)R$^7$; —C(O)N(R$^7$)(R$^8$); —C(O)N(R$^8$)(R$^9$); —C(O)OR$^7$; —SO$_2$N(R$^{10}$)—R$^7$; —N(R$^{10}$)SO$_2$—R$^7$; —S(O)$_m$—R$^7$; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$, —SO$_2$N(R$^{10}$)—R$^7$, —N(R$^{10}$)SO$_2$—R$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O)OR$^7$, —SO$_2$N(R$^{10}$)—R$^7$, —N(R$^{10}$)SO$_2$—R$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N (R$^8$)(R$^9$), —C(O)OR$^7$, —SO$_2$N(R$^{10}$)—R$^7$, —N(R$^{10}$)SO$_2$—R$^7$ or —S(O)$_m$—R$^7$;

R$^7$ is independently H; alkyl optionally substituted one or more times by halogen, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; cycloalkyl optionally substituted one or more times by halogen, alkyl, haloalkyl, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OH, —OR$^{10}$, —NR$^8$R$^9$, —CN, —N(R$^{10}$)C(O)R$^{10}$, —C(O)N(R$^8$)(R$^9$), —C(O)OR$^{10}$ or —S(O)$_m$—R$^{10}$; or heteroaryl optionally substituted one or more times by halogen, alkyl, haloalkyl, cycloalkyl, —OR$^{10}$, —NR$^8$R$^9$, —CN, —N(R$^9$)C(O)R$^{10}$, —C(O)N(R$^8$)(R$^9$), —C(O)OR$^{10}$ or —S(O)$_m$—R$^{10}$;

R$^8$ is independently H or alkyl;
R$^9$ is independently H or alkyl;
or R$^8$ and R$^9$ are joined together with the nitrogen to which they are attached
form a saturated 5- to 7-membered heterocyclic ring;
R$^{10}$ is independently H or alkyl;

R$^{11}$ is independently H; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O) OR$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

R$^{12}$ is independently H; alkyl optionally substituted one or more times by halogen, —OR$^7$, —NR$^8$R$^9$, —CN, —N(R$^{10}$)C(O)R$^7$, —C(O)N(R$^8$)(R$^9$), —C(O)OR$^7$ or —S(O)$_m$—R$^7$; cycloalkyl optionally substituted one or more times by halogen, alkyl, haloalkyl, —OR$^7$, —NR$^8$R$^9$, —CN, —N(R$^{10}$)C(O)R$^7$, —C(O)N(R$^8$)(R$^9$), —C(O)OR$^{10}$ or —S(O)$_m$—R$^{10}$; aryl optionally substituted one or more times by halogen, alkyl, haloalkyl, cycloalkyl, —OR$^7$, —CN, —NR$^8$R$^9$—N(R$^{10}$)C(O)(R$^7$), —C(O)N(R$^7$)(R$^8$), —C(O)OR$^7$ or —S(O)$_m$—R$^7$; heterocycloalkyl optionally substituted one or more times by halogen, alkyl, haloalkyl, —OR$^7$, —CN, —NR$^8$R$^9$—N(R$^{10}$)C(O)R$^7$, —C(O)N(R$^8$)(R$^9$), —C(O) OR$^7$ or —S(O)$_m$—R$^7$; or heteroaryl optionally substituted one or more times by halogen, alkyl, haloalkyl, cycloalkyl, —OR$^7$, —CN, —NR$^8$R$^9$, —N(R$^{10}$)C(O)R$^7$, —C(O)N(R$^8$)(R$^9$), —C(O)OR$^7$ or —S(O)$_m$—R$^7$;

a is 0, 1, 2, 3 or 4;
n is 1 or 2; and
m is 0, 1 or 2.

3. The compound as defined in claim 1 or a pharmaceutically acceptable salt thereof, which has the structural formula of Formula II

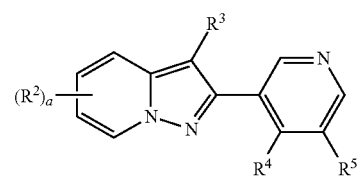

wherein:

R$^2$ is independently halogen, —CN, alkyl, haloalkyl, cycloalkyl, OR$^7$ or phenyl optionally substituted by halogen;

R$^3$ is H, halogen, —CN, alkyl, cycloalkyl or phenyl optionally substituted by halogen, alkyl, cycloalkyl or haloalkyl;

R$^4$ is H or alkyl;

R$^5$ is:

i.) halogen, —CN, cycloalkyl, —OR$^7$, haloalkyl or phenyl optionally substituted by halogen or haloalkyl; or alkyl substituted by halogen or haloalkyl or ii.) a group of the formula:

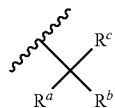

where:
- $R^a$ is H, OH, or —$C_1$-$C_3$-alkyl optionally substituted with 1 to 3-F;
- $R^b$ is H, —OH, or —$C_1$-$C_3$-alkyl optionally substituted with 1 to 3-F;
- $R^c$ is —$C_1$-$C_3$-alkyl optionally substituted with 1 to 3-F; —$OC_1$-$C_3$-alkyl; —$N(H)S(O)_2$—$C_1$-$C_3$-alkyl; optionally substituted with 1 to 3-F; or —$N(H)C(O)C_1$-$C_3$-alkyl, optionally substituted with 1 to 3-F;
- $R^7$ is H, alkyl, haloalkyl, cycloalkyl, or phenyl optionally substituted by halogen; and
- a is 0, 1 or 2.

4. A pharmaceutical composition comprising a therapeutically effective amount of at least one compound of Formula I as defined in claim 1 or a pharmaceutically acceptable salt thereof and a pharmaceutically acceptable carrier.

5. A pharmaceutical composition comprising a therapeutically effective amount of at least one compound of Formula I as defined in claim 1 or a pharmaceutically acceptable salt thereof, a therapeutically effective amount of at least one additional therapeutic agent and a pharmaceutically acceptable carrier.

* * * * *